(12) United States Patent
Chadeayne

(10) Patent No.: US 12,404,238 B2
(45) Date of Patent: Sep. 2, 2025

(54) PSILOCYBIN DERIVATIVES

(71) Applicant: CAAMTECH, INC., Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

(21) Appl. No.: 18/717,094

(22) PCT Filed: Dec. 12, 2022

(86) PCT No.: PCT/US2022/081343
§ 371 (c)(1),
(2) Date: Jun. 6, 2024

(87) PCT Pub. No.: WO2023/108167
PCT Pub. Date: Jun. 15, 2023

(65) Prior Publication Data
US 2024/0417373 A1    Dec. 19, 2024

Related U.S. Application Data

(60) Provisional application No. 63/330,473, filed on Apr. 13, 2022, provisional application No. 63/314,550, filed on Feb. 28, 2022, provisional application No. 63/288,000, filed on Dec. 10, 2021.

(51) Int. Cl.
C07D 209/14    (2006.01)

(52) U.S. Cl.
CPC ................. *C07D 209/14* (2013.01)

(58) Field of Classification Search
CPC .................................................. C07D 209/14
See application file for complete search history.

(56) References Cited

U.S. PATENT DOCUMENTS

| | | |
|---|---|---|
| 2018/0221396 A1 | 8/2018 | Chadeayne |
| 2019/0105313 A1 | 4/2019 | Stamets |
| 2019/0142851 A1 | 5/2019 | Chadeayne |
| 2021/0403425 A1 | 12/2021 | Bryson |

FOREIGN PATENT DOCUMENTS

| | | |
|---|---|---|
| WO | 2021/155470 A1 | 8/2021 |
| WO | 2021155468 A1 | 8/2021 |
| WO | 2022/000091 A1 | 1/2022 |
| WO | 2022/133314 A1 | 6/2022 |
| WO | 2023/133477 A1 | 7/2023 |

OTHER PUBLICATIONS

International Preliminary Report on Patentability dated Jun. 20, 2024 issued in PCT Application No. PCT/US2022/081343.
Dolomanov et al., (2009) "OLEX2: A complete structure solution, refinement and analysis program," J. Appl. Cryst. 42, 339-341.
Sheldrick, (2015) "Crystal structure refinement with SHELXL," Acta Cryst., C71, 3-8.
Thawabteh et al. "Bitterless Guaifenesin Prodrugs—Design, Synthesis, Characterization, In Vitro Kinestics and Bitternes Studies" Chem Biol Drug Des. 2019, vol. 93(3), p. 262-271.
Yang et al. "Crystal Structure, Stability and Desolvation of the Solvates of Sorafenib Tosylate" Crystals, 2019, vol. 9, p. 367-381.
Compound Summary: 4-Hydroxy-N, N-Diisopropyltryptamine. PubChem-CID-21854225, 2007.
International Search Report and Written Opinion of International Application No. PCT/US2022/081343, dated Mar. 30, 2023.
Stephen Byrn et al: "Pharmaceutical Solids: A strategic Approach to Regulatory Considerations", Pharmaceutical Research, Springer Berlin Heidelberg, Berlin/Heidelberg, vol. 12, No. 7, Jul. 1, 1995 (Jul. 1, 1995), pp. 945-954.
Mino R Caira Ed—Montchamp Jean-Luc: "Crystalline Polymorphism of Organic Compounds", Topics in Current Chemistry; [Topics in Current Chemistry], Springer, Berlin, DE, vol. 198, Jan. 1, 1998 (Jan. 1, 1998), pp. 163-208.

*Primary Examiner* — Shawquia Jackson
(74) *Attorney, Agent, or Firm* — RAPHAEL BELLUM PLLC

(57) ABSTRACT

The disclosure relates to forms of 5-[(3-{2-[bis(propan-2-yl)azaniumyl]ethyl}-1H-indol-4-yl)oxy]-5-oxopentanoate, including solvates such as methanol 5-[(3-{2-[bis(propan-2-yl)azaniumyl]ethyl}-1H-indol-4-yl)oxy]-5-oxopentanoate (also referred to as 4-glutarato-N,N-diisopropyltryptamine methanol solvate or 4-glutarato-DiPT-MeOH), and crystalline forms thereof such as crystalline form 1 of 4-glutarato-DiPT-MeOH and ethanol 5-[(3-{2-[bis(propan-2-yl)azaniumyl]ethyl}-1H-indol-4-yl)oxy]-5-oxopentanoate (4-glutarato-N,N-diisopropyltryptamine ethanol solvate or 4-glutarato-N,N-DiPT-EtOH), crystalline 4-glutarato-N,N-DiPT-EtOH, and crystalline forms thereof, including crystalline form 1 of 4-glutarato-N,N-DiPT-EtOH; and to pharmaceutical compositions containing them and to methods of treatment using them. The disclosure further relates to crystalline [3-[2-(methylamino)ethyl]-1H-indol-4-yl] dihydrogen phosphate (baeocystin), such as crystalline form 1 of baeocystin, and to pharmaceutical compositions containing crystalline baeocystin, such as crystalline form 1 of baeocystin, and to methods of treatment using it.

8 Claims, 8 Drawing Sheets

PSILOCYBIN DERIVATIVES

CROSS REFERENCE TO RELATED APPLICATIONS

This application claims priority to U.S. Provisional Application No. 63/288,000, filed on Dec. 10, 2021; U.S. Provisional Application No. 63/314,550, filed on Feb. 28, 2022; and U.S. Provisional Application No. 63/330,473, filed on Apr. 13, 2022; the disclosures of which are incorporated by reference.

TECHNICAL FIELD

This disclosure relates to forms of 5-[(3-{2-[bis(propan-2-yl)azaniumyl]ethyl}-1H-indol-4-yl)oxy]-5-oxopentanoate, including solvates such as methanol 5-[(3-{2-[bis(propan-2-yl)azaniumyl]ethyl}-1H-indol-4-yl)oxy]-5-oxopentanoate (also referred to as 4-glutarato-N,N-diisopropyltryptamine methanol solvate or 4-glutarato-DiPT·MeOH), and crystalline forms thereof, such as crystalline form 1 of 4-glutarato-DiPT·MeOH, to pharmaceutical compositions containing it, and to methods of treatment/therapeutic uses of them.

This disclosure further relates to ethanol 5-[(3-{2-[bis(propan-2-yl)azaniumyl]ethyl}-1H-indol-4-yl)oxy]-5-oxopentanoate (4-glutarato-N,N-diisopropyltryptamine ethanol solvate or 4-glutarato-N,N-DiPT·EtOH), crystalline 4-glutarato-N,N-DiPT·EtOH, and specific crystalline forms thereof, including crystalline form 1 of 4-glutarato-N,N-DiPT·EtOH; to pharmaceutical compositions containing 4-glutarato-N,N-DiPT·EtOH or crystalline 4-glutarato-N,N-DiPT·EtOH, including crystalline form 1 of 4-glutarato-N,N-DiPT·EtOH; and to methods of treatment/therapeutic uses of 4-glutarato-N,N-DiPT·EtOH or crystalline 4-glutarato-N,N-DiPT·EtOH, including crystalline form 1 of 4-glutarato-N,N-DiPT·EtOH.

This disclosure further relates to crystalline [3-[2-(methylamino)ethyl]-1H-indol-4-yl] dihydrogen phosphate (baeocystin), including crystalline form 1 of baeocystin, to pharmaceutical compositions containing it, and to methods of treatment/therapeutic uses of crystalline baeocystin.

BACKGROUND OF THE INVENTION

Obtaining crystalline forms of an active pharmaceutical ingredient (API) is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process. Additionally, preparing a crystalline API and solving its crystal structure provides the gold standard for chemical characterization and determining the molecular formula (and molecular weight) of the API. Accordingly, preparing a crystalline form with an accompanying crystal structure thereof prevents potential ambiguities and/or inaccuracies in the API's molecular weight. This is important because the API's molecular weight is used to calculate the concentration of compositions comprising that API. Thus, inaccuracies in molecular weight may lead to errors in the calculations pertaining to dosing, potency, toxicity, etc. in all downstream in vitro and in vivo assays that correlated the concentration of the API with a measured property. Accordingly, there remains a need to obtain and characterize crystalline forms of APIs, such as tryptamines and other psychedelic drug compounds.

SUMMARY OF THE INVENTION

This disclosure relates to forms of 5-[(3-{2-[bis(propan-2-yl)azaniumyl]ethyl}-1H-indol-4-yl)oxy]-5-oxopentanoate, including solvates such as methanol 5-[(3-{2-[bis(propan-2-yl)azaniumyl]ethyl}-1H-indol-4-yl)oxy]-5-oxopentanoate (also referred to as 4-glutarato-N,N-diisopropyltryptamine methanol solvate or 4-glutarato-DiPT·MeOH), and crystalline forms thereof such as crystalline form 1 of 4-glutarato-DiPT·MeOH. Crystalline form 1 of 4-glutarato-DiPT·MeOH may be characterized by at least one of: a monoclinic, $P2_1/c$ space group at a temperature of about 297 K; unit cell dimensions a=7.9531 (5) Å, b=13.4224 (7) Å, c=21.2015 (11) Å, and β=92.484 (2°); an x-ray powder diffraction (XRPD) pattern substantially similar to FIG. 3; and an X-ray powder diffraction pattern characterized by peaks at 8.3, 11.1, and 15.1° 2θ±0.2° 2θ.

The disclosure further relates to a composition comprising forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms such as crystalline form 1 of 4-glutarato-DiPT·MeOH, and an excipient.

The disclosure also provides a composition comprising forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms such as crystalline form 1 of 4-glutarato-DiPT·MeOH, as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone; and a pharmaceutically acceptable excipient.

The disclosure also relates to a method of preventing or treating a psychological disorder comprising the step of administering to a subject in need thereof a therapeutically effective amount of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, or a composition according to this disclosure.

The disclosure further relates to a method of preventing or treating inflammation and/or pain, preventing or treating a neurological disorder, modulating activity of a mitogen-activated protein kinase (MAPK), modulating neurogenesis, or modulating neurite outgrowth comprising the step of administering to a subject in need thereof a therapeutically effective amount of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and to administering a pharmaceutical composition or a composition according to the invention.

This disclosure further relates to ethanol 5-[(3-{2-[bis(propan-2-yl)azaniumyl]ethyl}-1H-indol-4-yl)oxy]-5-oxopentanoate (4-glutarato-N,N-diisopropyltryptamine ethanol solvate or 4-glutarato-N,N-DiPT·EtOH), crystalline 4-glutarato-N,N-DiPT·EtOH, and specific crystalline forms thereof. In one embodiment, this disclosure pertains to particular crystalline forms of 4-glutarato-N,N-DiPT·EtOH, including crystalline form 1 of 4-glutarato-N,N-DiPT·EtOH. In one embodiment, crystalline form 1 of 4-glutarato-N,N-DiPT·EtOH is characterized by at least one of: a monoclinic, $P2_{1/c}$ space group at a temperature of about 297(2) K; unit cell dimensions a=8.0087(12) Å, b=13.7968(17) Å, c=21.878(3) Å, α=90°, β=90.749(4°), and γ=90°; an X-ray powder diffraction (XRPD) pattern substantially similar to FIG. 6; and an X-ray powder diffraction pattern characterized by at least two peaks selected from 8.1, 11.0, and 17.0° 2θ±0.2° 2θ.

The disclosure further relates to a composition comprising 4-glutarato-N,N-DiPT·EtOH, crystalline 4-glutarato-N,N-DiPT·EtOH, or specific crystalline forms thereof, such as crystalline form 1 of 4-glutarato-N,N-DiPT·EtOH, and at least one excipient.

The disclosure also provides a composition comprising 4-glutarato-N,N-DiPT·EtOH, crystalline 4-glutarato-N,N-DiPT·EtOH, or specific crystalline forms thereof, such as crystalline form 1 of 4-glutarato-N,N-DiPT·EtOH, as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone; and at least one excipient.

The disclosure also relates to a method of preventing or treating a psychological disorder comprising the step of administering to a subject in need thereof a therapeutically effective amount of 4-glutarato-N,N-DiPT·EtOH, crystalline 4-glutarato-N,N-DiPT·EtOH, or specific crystalline forms thereof, such as crystalline form 1 of 4-glutarato-N,N-DiPT·EtOH, or a composition according to this disclosure.

The disclosure further relates to a method of preventing or treating inflammation and/or pain, preventing or treating a neurological disorder, modulating activity of a mitogen-activated protein kinase (MAPK), modulating neurogenesis, or modulating neurite outgrowth comprising the step of administering to a subject in need thereof a therapeutically effective amount of a compound of 4-glutarato-N,N-DiPT·EtOH, crystalline 4-glutarato-N,N-DiPT·EtOH, or specific crystalline forms thereof, such as crystalline form 1 of 4-glutarato-N,N-DiPT·EtOH, and to administering a pharmaceutical composition or a composition according to the invention.

This disclosure further relates to crystalline [3-[2-(methylamino)ethyl]-1H-indol-4-yl] dihydrogen phosphate (baeocystin), including crystalline form 1 of baeocystin. Crystalline form 1 of baeocystin may be characterized by at least one of: an orthorhombic, Pbca space group at a temperature of about 297 K; unit cell dimensions a=13.229 (1) Å, b=10.5551 (7) Å, c=17.8346 (13) A; an x-ray powder diffraction (XRPD) pattern substantially similar to FIG. 9; and an X-ray powder diffraction pattern characterized by peaks at 15.8, 17.5, 21.5° 2θ±0.2° 2θ.

The disclosure further relates to a composition comprising crystalline baeocystin according to this disclosure, such as crystalline form 1 of baeocystin, and an excipient.

The disclosure also provides a composition comprising crystalline baeocystin according to this disclosure, such as crystalline form 1 of baeocystin, as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone; and a pharmaceutically acceptable excipient.

The disclosure also relates to a method of preventing or treating a psychological disorder comprising the step of administering to a subject in need thereof a therapeutically effective amount of crystalline baeocystin according to this disclosure, such as crystalline form 1 of baeocystin, or a composition according to this disclosure.

The disclosure further relates to a method of preventing or treating inflammation and/or pain, preventing or treating a neurological disorder, modulating activity of a mitogen-activated protein kinase (MAPK), modulating neurogenesis, or modulating neurite outgrowth comprising the step of administering to a subject in need thereof a therapeutically effective amount of a compound of crystalline baeocystin according to this disclosure, such as crystalline form 1 of baeocystin, and to administering a pharmaceutical composition or a composition according to the invention.

As used herein, the term "a subject in need thereof" refers a person requiring a composition to treat a particular disease or condition (e.g., inflammation, pain, a psychological disorder, modulating activity at a receptor, etc.). In one embodiment, the "subject in need thereof" may be identified by analyzing, diagnosing, and/or determining whether the person (or subject) requires the composition for treatment of a particular disease or condition. In one embodiment, identifying a person in need of treatment comprises diagnosing a person with a medical condition, e.g., a neurological disorder, a chemical imbalance, a hereditary condition, etc. In one embodiment, identifying a person in need of treatment comprises performing a psychiatric evaluation. In one embodiment, identifying a person in need of treatment comprises performing a blood test. In one embodiment, identifying a person in need of treatment comprises determining whether a person has a compulsive disorder. In one embodiment, identifying a person in need of treatment comprises self-identifying as having a compulsive disorder.

DETAILED DESCRIPTION

Compounds

Figure 1:
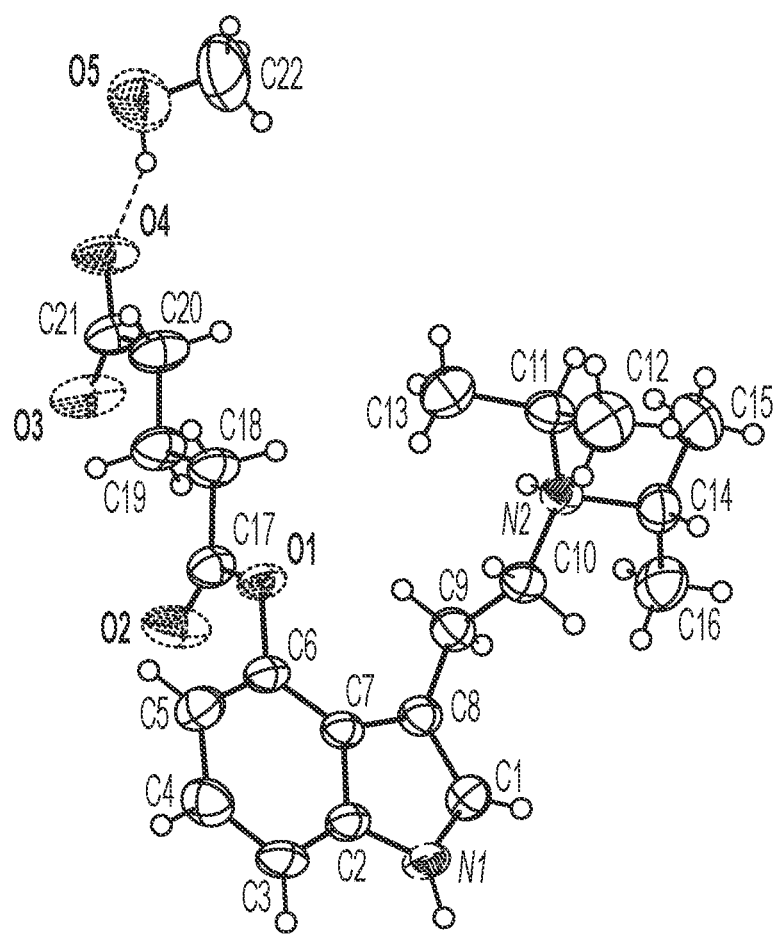
FIG. 1 shows the molecular structure of crystalline form 1 of 4-glutarato-DiPT·MeOH with atomic labeling; hydrogen bonds are shown as dashed lines.

This disclosure relates to forms of 5-[(3-{2-[bis(propan-2-yl)azaniumyl]ethyl}-1H-indol-4-yl)oxy]-5-oxopentanoate, including solvates such as methanol 5-[(3-{2-[bis(propan-2-yl)azaniumyl]ethyl}-1H-indol-4-yl)oxy]-5-oxopentanoate (4-glutarato-N,N-diisopropyltryptamine methanol solvate or 4-glutarato-DiPT·MeOH), and crystalline forms thereof such as such as crystalline form 1 of 4-glutarato-DiPT·MeOH, and to pharmaceutical compositions containing a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH. The therapeutic uses of forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, are described below as well as compositions containing them. Crystalline form 1 of 4-glutarato-DiPT·MeOH and the methods used to characterize it are described in the examples below.

In certain embodiments, the forms of 5-[(3-{2-[bis(propan-2-yl)azaniumyl]ethyl}-1H-indol-4-yl)oxy]-5-oxopentanoate include solvates selected from the following chemical structure:

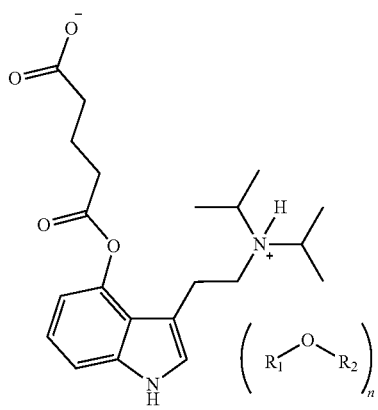

wherein $R_1$—O—$R_2$ is a coordinating solvent and n=1 to 4. In certain embodiments, $R_1$ and $R_2$ are independently selected from hydrogen, optionally substituted alkyl (e.g., $C_1$-$C_8$ alkyl), and optionally substituted saturated or unsaturated $C_1$-$C_8$ carbonyl or dicarbonyl. $R_1$ and $R_2$ may be a $C_1$-$C_4$ straight chain or branched alkyl. In certain embodiments, $R_1$ is hydrogen and $R_2$ is optionally substituted alkyl. Exemplary coordinating solvents include, but are not limited to, water, methanol, ethanol, propanol, isopropanol, fumaric acid, maleic acid, oxalic acid, succinic acid, glutaric acid, acetic acid, etc. In certain embodiments, the solvates are crystalline.

4-glutarato-DiPT·MeOH has the following chemical structure:

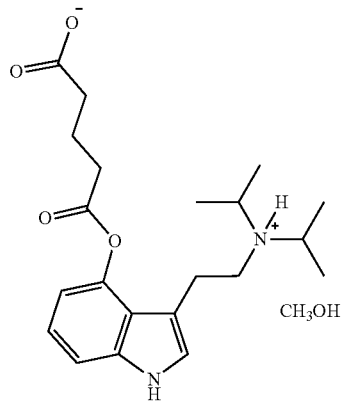

This disclosure further relates to ethanol 5-[(3-{2-[bis(propan-2-yl)azaniumyl]ethyl}-1H-indol-4-yl)oxy]-5-oxopentanoate (4-glutarato-N,N-diisopropyltryptamine ethanol solvate or 4-glutarato-N,N-DiPT·EtOH), crystalline 4-glutarato-N,N-DiPT·EtOH, and specific crystalline forms thereof, including crystalline form 1 of 4-glutarato-N,N-DiPT·EtOH, and to compositions containing 4-glutarato-N,N-DiPT·EtOH or crystalline 4-glutarato-N,N-DiPT·EtOH (such as crystalline form 1 of 4-glutarato-N,N-DiPT·EtOH) according to the disclosure. The therapeutic uses of 4-glutarato-N,N-DiPT·EtOH or crystalline 4-glutarato-N,N-DiPT·EtOH, including crystalline form 1 of 4-glutarato-N,N-DiPT·EtOH, according to the disclosure are described below as well as compositions containing them. 4-glutarato-N,N-DiPT·EtOH or crystalline 4-glutarato-N,N-DiPT·EtOH, including crystalline form 1 of 4-glutarato-N,N-DiPT·EtOH, and some exemplary methods used to characterize it are described below.

4-glutarato-N,N-DiPT·EtOH has the following chemical formula:

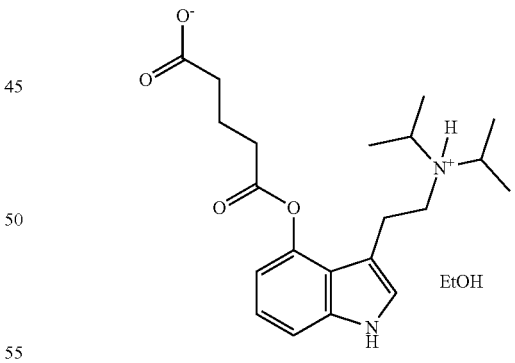

This disclosure further relates to crystalline [3-[2-(methylamino)ethyl]-1H-indol-4-yl] dihydrogen phosphate (baeocystin), such as crystalline form 1 of baeocystin, and to pharmaceutical compositions containing crystalline baeocystin according to the disclosure, such as crystalline form 1 of baeocystin. The therapeutic uses of crystalline baeocystin according to the disclosure, such as crystalline form 1 of baeocystin, are described below as well as compositions containing it. Crystalline form 1 of baeocystin and the methods used to characterize it are described in the examples below.

Baeocystin has the following chemical structure:

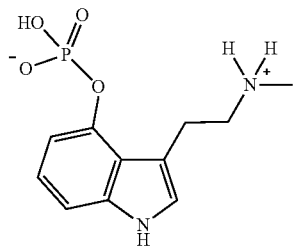 [SMILES: C[NH2+]CCc1c[nH]c2cccc(OP(=O)([O-])O)c12]

Methods of Treatment and Therapeutic Uses

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and the methods and the compositions (e.g., pharmaceutical compositions) are used to regulate the activity of a neurotransmitter receptor by administering a therapeutically effective dose of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH. In one embodiment, a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and the methods and the compositions (e.g., pharmaceutical compositions) are used to treat inflammation and/or pain by administering a therapeutically effective dose of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH.

Methods of the disclosure also relate to the administration of a therapeutically effective amount of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, to prevent or treat a disease or condition, such as those discussed below for a subject in need of treatment. A form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be administered neat or as a composition comprising a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, as discussed below.

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used to prevent and/or treat a psychological disorder. The disclosure provides a method for preventing and/or treating a psychological disorder by administering to a subject in need thereof a therapeutically effective amount of a form of 5-[(3-{2-[bis(propan-2-yl)azaniumyl]ethyl}-1H-indol-4-yl)oxy]-5-oxopentanoate, including solvates such as 4-glutarato-DiPT·MeOH, including solvates such as 4-glutarato-DiPT·MeOH according to this disclosure, and crystalline forms thereof, such as crystalline form 1 of 4-glutarato-DiPT·MeOH, including the exemplary embodiments discussed herein. The psychological disorder may be chosen from depression; psychotic disorder; schizophrenia; schizophreniform disorder (acute schizophrenic episode); schizoaffective disorder; bipolar I disorder (mania, manic disorder, manic-depressive psychosis); bipolar 11 disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome; post-traumatic stress disorder (PTSD); premenstrual dysphoric disorder (PMDD); and premenstrual syndrome (PMS).

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used to prevent and/or treat a brain disorder. The disclosure provides a method for preventing and/or treating a brain disorder (e.g., Huntington's disease, Alzheimer's disease, dementia, and Parkinson's disease) by administering to a subject in need thereof a therapeutically effective amount of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, including the exemplary embodiments discussed above.

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, including the exemplary embodiments discussed above.

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, including the exemplary embodiments discussed herein. Generally speaking, for the purposes of this disclosure, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e., mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used to modulate activity of a mitogen-activated protein kinase (MAPK), comprising administering a composition of the invention. MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-a. In the central nervous system, p38-alpha regulates neuronal death and neurite degeneration, and it is a common target of Alzheimer's disease therapies. JNK3 is a neuronal specific protein isoform of the JNKs. It is involved with the regulation of apoptosis. JNK3 also plays a role in modulating the response of cytokines, growth factors, and oxidative stress.

As used herein, for the purposes of this disclosure, the term "modulating activity of a mitogen-activated protein kinase" refers to changing, manipulating, and/or adjusting the activity of a mitogen-activated protein kinase. In one embodiment, modulating the activity of a MAPK can influence neural health, neurogenesis, neural growth and differentiation, and neurodegenerative diseases.

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used to modulate neurogenesis, comprising administering a composition of the invention. As used herein, the term "modulating neurogenesis" refers to changing, manipulating, and/or adjusting the growth and development of neural tissue. In one embodiment, neurogenesis comprises adult neurogenesis, in which new neural stem cells are generated from neural stem cells in an adult animal. In one embodiment, modulating neurogenesis comprises increasing and/or enhancing the rate at which new neural tissue is developed.

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used to modulate neurite outgrowth, comprising administering a composition of the invention. As used herein, the term "modulating neurite outgrowth" refers to changing, manipulating, and/or adjusting the growth and development of neural projections, or "neurites." In one embodiment, neurogenesis comprises modulating the growth of new neurites, the number of neurites per neuron, and/or neurite length. In one embodiment, modulating neurite outgrowth comprises increasing and/or enhancing the rate and/or length at which neurites develop.

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used to prevent and/or treat sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used to prevent and/or treat women's health disorders including, but not limited to, menstrual cramping, dysmenorrhea, post-hysterectomy pain, vaginal or vulvar vestibule mucosa disorder, menopausal-related disorders, vaginal atrophy, or vulvar vestibulitis.

4-glutarato-N,N-DiPT·EtOH or crystalline 4-glutarato-N,N-DiPT·EtOH (such as crystalline form 1 of 4-glutarato-N,N-DiPT·EtOH) according to the disclosure, and the methods and the compositions (e.g., pharmaceutical compositions) thereof, are used to regulate the activity of a neurotransmitter receptor by administering a therapeutically effective dose of 4-glutarato-N,N-DiPT·EtOH or crystalline 4-glutarato-N,N-DiPT·EtOH, such as crystalline form 1 of 4-glutarato-N,N-DiPT·EtOH, of the disclosure. In one embodiment, 4-glutarato-N,N-DiPT·EtOH or crystalline 4-glutarato-N,N-DiPT·EtOH, such as crystalline form 1 of 4-glutarato-N,N-DiPT·EtOH, according to the disclosure, and the methods and the compositions (e.g., pharmaceutical compositions) are used to treat inflammation and/or pain by administering a therapeutically effective dose of 4-glutarato-N,N-DiPT·EtOH or crystalline 4-glutarato-N,N-DiPT·EtOH, such as crystalline form 1 of 4-glutarato-N,N-DiPT·EtOH, of the disclosure.

Methods of the disclosure also relate to the administration of a therapeutically effective amount of 4-glutarato-N,N-DiPT·EtOH or crystalline 4-glutarato-N,N-DiPT·EtOH, such as crystalline form 1 of 4-glutarato-N,N-DiPT·EtOH, to prevent or treat a disease or condition, such as those discussed below for a subject in need of treatment. 4-glutarato-N,N-DiPT·EtOH or crystalline 4-glutarato-N,N-DiPT·EtOH, such as crystalline form 1 of 4-glutarato-N,N-DiPT·EtOH, may be administered neat or as a composition comprising 4-glutarato-N,N-DiPT·EtOH or crystalline 4-glutarato-N,N-DiPT·EtOH, such as crystalline form 1 of 4-glutarato-N,N-DiPT·EtOH, as discussed below.

4-glutarato-N,N-DiPT·EtOH or crystalline 4-glutarato-N,N-DiPT·EtOH, such as crystalline form 1 of 4-glutarato-N,N-DiPT·EtOH, of the disclosure may be used to prevent and/or treat a psychological disorder. The disclosure provides a method for preventing and/or treating a psychological disorder by administering to a subject in need thereof a therapeutically effective amount of 4-glutarato-N,N-DiPT·EtOH or crystalline 4-glutarato-N,N-DiPT·EtOH, such as crystalline form 1 of 4-glutarato-N,N-DiPT·EtOH, of the disclosure, including the exemplary embodiments discussed herein. The psychological disorder may be chosen from depression; psychotic disorder; schizophrenia; schizophreniform disorder (acute schizophrenic episode); schizoaffective disorder; bipolar I disorder (mania, manic disorder, manic-depressive psychosis); bipolar 11 disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome; post-traumatic stress disorder (PTSD); premenstrual dysphoric disorder (PMDD); and premenstrual syndrome (PMS).

4-glutarato-N,N-DiPT·EtOH or crystalline 4-glutarato-N,N-DiPT·EtOH, such as crystalline form 1 of 4-glutarato-N,N-DiPT·EtOH, of the disclosure may be used to prevent and/or treat a brain disorder. The disclosure provides a method for preventing and/or treating a brain disorder (e.g., Huntington's disease, Alzheimer's disease, dementia, and Parkinson's disease) by administering to a subject in need thereof a therapeutically effective amount of 4-glutarato-N,N-DiPT·EtOH or crystalline 4-glutarato-N,N-DiPT·EtOH, such as crystalline form 1 of 4-glutarato-N,N-DiPT·EtOH.

4-glutarato-N,N-DiPT·EtOH or crystalline 4-glutarato-N,N-DiPT·EtOH, such as crystalline form 1 of 4-glutarato-N,N-DiPT·EtOH, of the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of 4-glutarato-N,N-DiPT·EtOH or crystalline 4-glutarato-N,N-DiPT·EtOH, such as crystalline form 1 of 4-glutarato-N,N-DiPT·EtOH, including the exemplary embodiments discussed above.

4-glutarato-N,N-DiPT·EtOH or crystalline 4-glutarato-N,N-DiPT·EtOH, such as crystalline form 1 of 4-glutarato-N,N-DiPT·EtOH, of the disclosure may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of 4-glutarato-N,N-DiPT·EtOH or crystalline 4-glutarato-N,N-DiPT·EtOH, such as crystalline form 1 of 4-glutarato-N,N-DiPT·EtOH, of the disclosure, including the exemplary embodiments discussed herein.

4-glutarato-N,N-DiPT·EtOH or crystalline 4-glutarato-N,N-DiPT·EtOH, such as crystalline form 1 of 4-glutarato-N,N-DiPT·EtOH, of the disclosure may be used to modulate activity of a mitogen-activated protein kinase (MAPK), as disclosed above, comprising administering a composition of the invention. MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-α. In the central nervous system, p38-alpha regulates neuronal death and neurite degeneration, and it is a common target of Alzheimer's disease therapies. JNK3 is a neuronal-specific protein isoform of the JNKs. It is involved with the regulation of apoptosis. JNK3 also plays a role in modulating the response of cytokines, growth factors, and oxidative stress.

4-glutarato-N,N-DiPT·EtOH or crystalline 4-glutarato-N,N-DiPT·EtOH, such as crystalline form 1 of 4-glutarato-N,N-DiPT·EtOH, of the disclosure may be used to modulate neurogenesis, as disclosed above, comprising administering a composition of the invention.

4-glutarato-N,N-DiPT·EtOH or crystalline 4-glutarato-N,N-DiPT·EtOH, such as crystalline form 1 of 4-glutarato-N,N-DiPT·EtOH, of the disclosure may be used to modulate neurite outgrowth, as disclosed above, comprising administering a composition of the invention.

4-glutarato-N,N-DiPT·EtOH or crystalline 4-glutarato-N,N-DiPT·EtOH, such as crystalline form 1 of 4-glutarato-N,N-DiPT·EtOH, of the disclosure may be used for preventing or treating sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

4-glutarato-N,N-DiPT·EtOH or crystalline 4-glutarato-N,N-DiPT·EtOH, such as crystalline form 1 of 4-glutarato-N,N-DiPT·EtOH, of the disclosure may be used for preventing or treating women's health disorders including, but not limited to, menstrual cramping, dysmenorrhea, post-hysterectomy pain, vaginal or vulvar vestibule mucosa disorder, menopausal-related disorders, vaginal atrophy, or vulvar vestibulitis.

Crystalline baeocystin according to this disclosure, such as crystalline form 1 of baeocystin, and the methods and the compositions (e.g., pharmaceutical compositions) are used to regulate the activity of a neurotransmitter receptor by administering a therapeutically effective dose of crystalline baeocystin of the disclosure, such as crystalline form 1 of baeocystin. In one embodiment, crystalline baeocystin according to the disclosure, such as crystalline form 1 of baeocystin, and the methods and the compositions (e.g., pharmaceutical compositions) are used to treat inflammation and/or pain by administering a therapeutically effective dose of crystalline baeocystin of the disclosure, such as crystalline form 1 of baeocystin.

Methods of the disclosure also related to the administration of a therapeutically effective amount of crystalline baeocystin, such as crystalline form 1 of baeocystin, to prevent or treat a disease or condition, such as those discussed below for a subject in need of treatment. Crystalline baeocystin, such as crystalline form 1 of baeocystin, may be administered neat or as a composition comprising crystalline baeocystin, such as crystalline form 1 of baeocystin, as discussed below.

Crystalline baeocystin according to this disclosure, such as crystalline form 1 of baeocystin, may be used to prevent and/or treat a psychological disorder. The disclosure provides a method for preventing and/or treating a psychological disorder by administering to a subject in need thereof a therapeutically effective amount of crystalline baeocystin, such as crystalline form 1 of baeocystin, including the exemplary embodiments discussed herein. The psychological disorder may be chosen from depression; psychotic disorder; schizophrenia; schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome; post-traumatic stress disorder (PTSD); premenstrual dysphoric disorder (PMDD); and premenstrual syndrome (PMS).

Crystalline baeocystin according to this disclosure, such as crystalline form 1 of baeocystin, may be used to prevent and/or treat a brain disorder. The disclosure provides a method for preventing and/or treating a brain disorder (e.g., Huntington's disease, Alzheimer's disease, dementia, and Parkinson's disease) by administering to a subject in need thereof a therapeutically effective amount of crystalline baeocystin, such as crystalline form 1 of baeocystin, including the exemplary embodiments discussed above.

Crystalline baeocystin according to this disclosure, such as crystalline form 1 of baeocystin, may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of crystalline baeocystin, such as crystalline form 1 of baeocystin, including the exemplary embodiments discussed above.

Crystalline baeocystin according to this disclosure, such as crystalline form 1 of baeocystin, may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of crystalline baeocystin, such as crystalline form 1 of baeocystin, including the exemplary embodiments discussed herein.

Crystalline baeocystin according to this disclosure, such as crystalline form 1 of baeocystin, may be used to modulate activity of a mitogen-activated protein kinase (MAPK), as disclosed above, comprising administering a composition of the invention. MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-α. In the central nervous system, p38-alpha regulates neuronal death and neurite degeneration, and it is a common target of Alzheimer's disease therapies. JNK3 is neuronal specific protein isoform of the JNKs. It is involved with the regulation of apoptosis. JNK3 also plays a role in modulating the response of cytokines, growth factors, and oxidative stress.

Crystalline baeocystin according to this disclosure, such as crystalline form 1 of baeocystin, may be used to modulate neurogenesis, as disclosed above, comprising administering a composition of the invention.

Crystalline baeocystin according to this disclosure, such as crystalline form 1 of baeocystin, may be used to modulate neurite outgrowth, as disclosed above, comprising administering a composition of the invention.

Crystalline baeocystin according to this disclosure, such as crystalline form 1 of baeocystin may be used to prevent and/or treat sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

Crystalline baeocystin according to this disclosure, such as crystalline form 1 of baeocystin may be used to prevent and/or treat women's health disorders including, but not limited to, menstrual cramping, dysmenorrhea, post hysterectomy pain, vaginal or vulvar vestibule mucosa disorder, menopausal-related disorders, vaginal atrophy, or vulvar vestibulitis.

Other Uses

Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used as a component in biological or biochemical assays, as a research tool or standard, or as a process intermediate.

4-glutarato-N,N-DiPT·EtOH or crystalline 4-glutarato-N,N-DiPT·EtOH, such as crystalline form 1 of 4-glutarato-N,N-DiPT·EtOH, of the disclosure may be used as a component in biological or biochemical assays, as a research tool or standard, or as a process intermediate.

Compositions

The disclosure also relates to compositions comprising an effective amount of forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, including its exemplary embodiments discussed above, and an excipient (e.g., a pharmaceutically-acceptable excipient). In another embodiment, the disclosure also relates to pharmaceutical compositions comprising a therapeutically effective amount of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, including its exemplary embodiments discussed above, and a pharmaceutically acceptable excipient (also known as a pharmaceutically acceptable carrier). As discussed above, a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be, for example, therapeutically useful to prevent and/or treat the psychological disorders, brain disorders, pain, and inflammation as well as the other disorders described herein.

A composition or a pharmaceutical composition of the disclosure may be in any form which contains forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH. The composition may be, for example, a tablet, capsule, liquid suspension, injectable, topical, or transdermal. The compositions generally contain, for example, about 1% to about 99% by weight of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and, for example, 99% to 1% by weight of at least one suitable pharmaceutically acceptable excipient. In one embodiment, the composition may be between about 5% and about 75% by weight of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, with the rest being at least one suitable pharmaceutically acceptable excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used as the "first purified psilocybin derivative" in the compositions described in US 2018/0221396 A1 and US 2019/0142851 A1. Accordingly, this disclosure provides a composition comprising: a first component comprising a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH; at least one second component selected from at least one of (a) a serotonergic drug, (b) a purified psilocybin derivative, (c) a purified cannabinoid or (d) a purified terpene; and at least one pharmaceutically-acceptable excipient or at least one other adjuvant. Such a composition may be a pharmaceutical composition wherein the components are present individually in therapeutically effective amounts or by combination in a therapeutically effective amount to treat a disease, disorder, or condition as described herein.

When used in such compositions as a first component comprising forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, with a second component selected from at least one of (a) a serotonergic drug, (b) a purified psilocybin derivative, (c) a purified cannabinoid, or (d) a purified terpene, the compositions represent particular embodiments of the invention. Compositions having as a first component at least one of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, with a second component selected from at least one of (e) an adrenergic drug, (f) a dopaminergic drug, (g) a monoamine oxidase inhibitor, (h) a purified erinacine, (i) a purified hericenone represent additional particular embodiments of the invention represented by the compositions having a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

Within the context of this disclosure, the term "purified" means separated from other materials, such as plant or fungal material, e.g., protein, chitin, cellulose, or water. In one embodiment, the term "purified" refers to a compound substantially free of other materials. In one embodiment, the term "purified" refers to a compound that is substantially free from a second tryptamine compound. In one embodiment, the term "purified" refers to a compound substantially free from histidine. In one embodiment, the term "purified" refers to a compound substantially free from a biological material, such as mold, fungus, plant matter, or bacteria. In one embodiment, the term "purified" refers to a compound substantially free from a paralytic.

In one embodiment, the term "purified" refers to a compound which has been separated from other compounds that are typically co-extracted when the purified compound is extracted from a naturally occurring organism. In one embodiment, a "purified" psilocybin derivative is partially or completely isolated from other psilocybin derivatives present in a source material, such as a psilocybin-containing mushroom. In one example, "purified" baeocystin is substantially free from psilocybin and/or psilocin. By contrast, traditional psilocybin mushroom extracts (aka crude extracts or fruit body extracts) would be expected to contain an unpredictable and varying amount of psilocybin, psilocin, baeocystin, norbaeocystin, salts thereof, or combinations thereof. Other examples of unpurified psilocybin derivatives would include mycelium containing psilocybin derivatives and/or naturally occurring fungal material such as biological material and/or structural material such as chitin. Similarly, the term "*cannabis* extracts" or "cannabinoid extracts" traditionally refers to whole plants (aka crude or full spectrum extracts) which have not been subjected to further purification to eliminate unwanted molecules that naturally occur in the *cannabis* plant. For example, a "*cannabis* extract comprising cannabidiol" could be expected to include cannabidiol (aka "CBD") and also varying amounts of other compounds, including cannabinoids, terpenes, and other biological material.

In one embodiment, the term "purified" refers to a compound or composition that has been crystallized.

In one embodiment, the term "purified" refers to a compound or composition that has been chromatographed, for example by gas chromatography, liquid chromatography (e.g., LC, HPLC, etc.), etc.

In one embodiment, the term "purified" refers to a compound or composition that has been distilled.

In one embodiment, the term "purified" refers to a compound or composition that has been sublimed.

In one embodiment, the term "purified" refers to a compound or composition that has been subject to two or more steps chosen from crystallization, chromatography, distillation, or sublimation.

In one embodiment, the term "purified" refers to a compound that is between 80-100% pure.

In one embodiment, the term "purified" refers to a compound that is between 90-100% pure.

In one embodiment, the term "purified" refers to a compound that is between 95-100% pure.

In one embodiment, the term "purified" refers to a compound that is between 99-100% pure.

In one embodiment, the term "purified" refers to a compound that is between 99.9-100% pure.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated herein by reference. Exemplary psilocybin derivatives include but are not limited to psilocybin itself and the psilocybin derivates described in paragraphs [0081]-[0109] of US 2018/0221396 A1 and [0082]-[0110] US 2019/0142851 A1 as well as the disclosed exemplary embodiments. Exemplary cannabinoids include but are not limited to the cannabinoids described in paragraphs [0111]-[0145] of US 2018/0221396 A1 and [0112]-[0146] US 2019/0142851 A1 as well as the disclosed exemplary embodiments. Exemplary terpenes include but are not limited to the terpenes described in paragraphs [0160]-[0238] of US 2018/0221396 A1 and [0161]-[0300] US 2019/0142851 A1 as well as the disclosed exemplary embodiments.

A pharmaceutical formulation of the disclosure may comprise, consist essentially of, or consist of (a) forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and (c) a pharmaceutically acceptable excipient. In some embodiments, a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and the second active compound(s) are each present in a therapeutically effective amount using a purposefully engineered and unnaturally occurring molar ratios. Exemplary molar ratios of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. According to this disclosure a composition containing a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be used in place of a "purified psilocybin derivative" in the compositions described in US 2018/0221396 A1 and US 2019/0142851 A1. Accordingly, the disclosure provides a pharmaceutical formulation comprising as (a) at least one of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and at least one second component selected from (a) a purified psilocybin derivative, (b) a purified cannabinoid or (c) a purified terpene; and at least one pharmaceutically-acceptable excipient or at least one other adjuvant, as described herein. Such a composition may be a pharmaceutical composition wherein the components are present individually in therapeutically effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments. Some exemplary serotonergic drugs include SSRIs and SNRIs. Some examples of specific serotonergic drugs include the following molecules, including any salts, solvates, or polymorphs thereof: 6-allyl-N,N- diethyl-NL; N,N-dibutyl-T; N,N-diethyl-T; N,N-diisopropyl-T; 5-methyoxy-alpha-methyl-T; N,N-dimethyl-T; 2,alpha-dimethyl-T; alpha,N-dimethyl-T; N,N-dipropyl-T; N-ethyl-N-isopropyl-T; alpha-ethyl-T; 6-N,N-triethyl-NL; 3,4-dihydro-7-methoxy-1-methyl-C; 7-methyoxy-1-methyl-C; N,N-dibutyl-4-hydroxy-T; N,N-diethyl-4-hydroxy-T; N,N-diisopropyl-4-hydroxy-T; N,N-dimethyl-4-hydroxy-T; N,N-dimethyl-5-hydroxy-T; N,N-dipropyl-4-hydroxy-T; N-ethyl-4-hydroxy-N-methyl-T; 4-hydroxy-N-isopropyl-N-methyl-T; 4-hydroxy-N-methyl-N-propyl-T; 4-hydroxy-N,N-tetramethylene-T; ibogaine; N,N-diethyl-L; N-butyl-N-methyl-T; N,N-diisopropyl-4,5-methylenedioxy-T; N,N-diisopropyl-5,6-methylenedioxy-T; N,N-dimethyl-4,5-methylenedioxy-T; N,N-dimethyl-5,6-methylenedioxy-T; N-isopropyl-N-methyl-5,6-methylenedioxy-T; N,N-diethyl-2-methyl-T; 2-N,N-trimethyl-T; N-acetyl-5-methoxy-T; N,N-diethyl-5-methoxy-T; N,N-diisopropyl-5-methoxy-T; 5-methoxy-N,N-dimethyl-T; N-isopropyl-4-methoxy-N-methyl-T; N-isopropyl-5-methoxy-N-methyl-T; 5,6-dimethoxy-N-isopropyl-N-methyl-T; 5-methoxy-N-methyl-T; 5-methoxy-N,N-tetramethylene-T; 6-methoxy-1-methyl-1,2,3,4-tetrahydro-C; 5-methoxy-2-N,N-trimethyl-T; N,N-dimethyl-5-methylthio-T; N-isopropyl-N-methyl-T; alpha-methyl-T; N-ethyl-T; N-methyl-T; 6-propyl-NL; N,N-tetramethylene-T; tryptamine; 7-methoxy-1-methyl-1,2,3,4-tetrahydro-C; and alpha,N-dimethyl-5-methoxy-T. For additional information regarding these compounds see Shulgin, A.

T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In an exemplary embodiment, the serotonergic drug is 3,4-methylenedioxymethamphetamine.

Exemplary psilocybin derivatives include but are not limited to psilocybin itself and the psilocybin derivates described in paragraphs [0081]-[0109] of US 2018/0221396 A1 and [0082]-[0110] US 2019/0142851 A1 as well as the disclosed exemplary embodiments. In one embodiment, the compositions disclosed herein comprise one or more purified psilocybin derivatives chosen from: [3-(2-dimethylaminoethyl)-1H-indol-4-yl] dihydrogen phosphate; 4-hydroxytryptamine; 4-hydroxy-N,N-dimethyltryptamine; [3-(2-methylaminoethyl)-1H-indol-4-yl] dihydrogen phosphate; 4-hydroxy-N-methyltryptamine; [3-(aminoethyl)-1H-indol-4-yl] dihydrogen phosphate; [3-(2-trimethylaminoethyl)-1H-indol-4-yl] dihydrogen phosphate; and 4-hydroxy-N,N,N-trimethyltryptamine.

Exemplary cannabinoids include but are not limited to the cannabinoids described in paragraphs [0111]-[0145] of US 2018/0221396 A1 and [0112]-[0146] US 2019/0142851 A1 as well as the disclosed exemplary embodiments, incorporated here by reference. Examples of cannabinoids within the context of this disclosure include the following molecules: cannabichromene (CBC); cannabichromenic acid (CBCA); cannabichromevarin (CBCV); cannabichromevarinic acid (CBCVA); cannabicyclol (CBL); cannabicyclolic acid (CBLA); cannabicyclovarin (CBLV); cannabidiol (CBD); cannabidiol monomethylether (CBDM); cannabidiolic acid (CBDA); cannabidiorcol (CBD-C1); cannabidivarin (CBDV); cannabidivarinic acid (CBDVA); cannabielsoic acid B (CBEA-B); cannabielsoin (CBE); cannabielsoin acid A (CBEA-A); cannabigerol (CBG); cannabigerol monomethylether (CBGM); cannabigerolic acid (CBGA); cannabigerolic acid monomethylether (CBGAM); cannabigerovarin (CBGV); cannabigerovarinic acid (CBGVA); cannabinodiol (CBND); cannabinodivarin (CBVD); cannabinol (CBN); cannabinol methylether (CBNM); cannabinol-C2 (CBN-C2); cannabinol-C4 (CBN-C4); cannabinolic acid (CBNA); cannabiorcol (CBN-C1); cannabivarin (CBV); cannabitriol (CBT); cannabitriolvarin (CBTV); 10-ethoxy-9-hydroxy-delta-6a-tetrahydrocannabinol; cannabicitran (CBTC); cannabiripsol (CBR); 8,9-dihydroxy-delta-6a-tetrahydrocannabinol; delta-8-tetrahydrocannabinol (Δ8-THC); delta-8-tetrahydrocannabinolic acid (Δ8-THCA); delta-9-tetrahydrocannabinol (THC); delta-9-tetrahydrocannabinol-C4 (THC-C4); delta-9-tetrahydrocannabinolic acid A (THCA-A); delta-9-tetrahydrocannabinolic acid B (THCA-B); delta-9-tetrahydrocannabinolic acid-C4 (THCA-C4); delta-9-tetrahydrocannabiorcol (THC-C1); delta-9-tetrahydrocannabiorcolic acid (THCA-C1); delta-9-tetrahydrocannabivarin (THCV); delta-9-tetrahydrocannabivarinic acid (THCVA); 10-oxo-delta-6a-tetrahydrocannabinol (OTHC); cannabichromanon (CBCF); cannabifuran (CBF); cannabiglendol; delta-9-cis-tetrahydrocannabinol (cis-THC); trihydroxy-delta-9-tetrahydrocannabinol (triOH-THC); dehydrocannabifuran (DCBF); and 3,4,5,6-tetrahydro-7-hydroxy-alpha-alpha-2-trimethyl-9-n-propyl-2,6-methano-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed exemplary embodiments. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant. In one embodiment, an adrenergic drug is a norepinephrine transporter inhibitor. In one embodiment, an adrenergic drug is a vesicular monoamine transporter inhibitor. In one embodiment, an adrenergic drug is chosen from adrenaline, agmatine, amoxapine, aptazapine, atomoxetine, bupropion, clonidine, doxepin, duloxetine, esmirtazpine, mianserin, ketanserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor. In one embodiment, a dopaminergic drug is a vesicular monoamine transporter inhibitor. In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

As used herein, the term "monoamine oxidase inhibitor" (MAOI) refers to a compound that blocks the actions of monoamine oxidase enzymes. In one embodiment, a MAOI inhibits the activity of one or both monoamine oxidase A and monoamine oxidase B. In one embodiment a MAOI is a reversible inhibitors of monoamine oxidase A. In one embodiment a MAOI is a drug chosen from isocarboxazid, phenelzine, or tranylcypromine. In one embodiment, a MAOI is β-carboline, pinoline, harmane, harmine, harmaline, harmalol, tetrahydroharmine, 9-methyl-β-carboline, or 3-carboxy-tetrahydrononharman.

In one embodiment, the compositions and methods disclosed herein include one or more purified erinacine molecules. In one embodiment, the compositions and methods disclosed herein comprise purified erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D. In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine J. In one embodiment, the compositions and methods disclosed herein comprise erinacine K In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S.

In one embodiment, the compositions and methods disclosed herein include one or more purified hericenone molecules. In one embodiment, the compositions and methods disclosed herein comprise purified hericenone A. In one embodiment, the compositions and methods disclosed herein comprise purified hericenone B. In one embodiment, the compositions and methods disclosed herein comprise purified hericenone C. In one embodiment, the compositions and methods disclosed herein comprise purified hericenone D. In one embodiment, the compositions and methods disclosed herein comprise purified hericenone E. In one embodiment, the compositions and methods disclosed herein comprise purified hericenone F. In one embodiment, the compositions and methods disclosed herein comprise purified hericenone G. In one embodiment, the compositions and methods disclosed herein comprise purified hericenone H.

Exemplary compositions of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone in exemplary molar ratios are shown in Table 1. Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be any one of the exemplary embodiments described above including the crystalline form of those compounds as disclosed herein.

TABLE 1

| Second Compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound |
|---|---|---|---|
| 3,4-methylenedioxy-methamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| Duloxetine | About 1:100 to about 100:1 | About 1:25 to about 25:1 | About 1:5 to about 5:1 |
| [3-(2-dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |

TABLE 1-continued

| Second Compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound |
|---|---|---|---|
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

Exemplary pharmaceutical compositions of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and an excipient with exemplary molar ratios of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, according to the second compound are shown in Table 2. Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be any one of the exemplary embodiments described above including the crystalline form as disclosed herein.

TABLE 2

| Second Compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound |
|---|---|---|---|
| 3,4-methylenedioxy-methamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| Duloxetine | About 1:100 to about 100:1 | About 1:25 to about 25:1 | About 1:5 to about 5:1 |
| [3-(2-dimethylaminoethyl)-1H-indol-4-yl] dihydrogen phosphate | About 1:100 to about 100:1 | About 1:25 to about 25:1 | About 1:5 to about 5:1 |

TABLE 2-continued

| Second Compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound | Molar ratio of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH: second compound |
| --- | --- | --- | --- |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

An "effective amount" or a "therapeutically effective amount" of a form of 5-[(3-{2-[bis(propan-2-yl)azaniumyl]ethyl}-1H-indol-4-yl)oxy]-5-oxopentanoate, including solvates such as 4-glutarato-DiPT•MeOH according to this disclosure, and crystalline forms thereof, such as crystalline form 1 of 4-glutarato-DiPT•MeOH, is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. Forms of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, and pharmaceutical compositions containing it may be used in combination with other agents that are generally administered to a patient being treated for psychological and other disorders discussed above. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Exemplary carriers include those that do not substantially alter the structure or activity of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, or produce undesirable biological effects or otherwise interact in a deleterious manner with any other component(s) of the pharmaceutical composition.

The pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginate, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. In some embodiments, the excipient is not water. In some embodiments, the excipient is not a solvent (e.g., EtOH, diethyl ether, ethyl acetate, or hydrocarbon-based solvents (e.g., hexanes). In some embodiments, the dosage form is substantially free of water and/or solvents, for example less than about 5% water by mass, less than 2% water by mass, less than 1% water by mass, less than 0.5% water by mass, or less than 0.1% water by mass.

Excipients or pharmaceutically acceptable adjuvants known in the pharmaceutical formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms of the disclosure may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions of the disclosure, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration of the disclosure, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of a form of 5-[(3-{2-[bis(propan-2-yl)azaniumyl]ethyl}-1H-indol-4-yl)oxy]-5-oxopentanoate, including solvates such as 4-glutarato-DiPT·MeOH according to this disclosure, and crystalline forms thereof, such as crystalline form 1 of 4-glutarato-DiPT·MeOH, in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

The disclosure also relates to compositions comprising an effective amount of 4-glutarato-N,N-DiPT·EtOH or crystalline 4-glutarato-N,N-DiPT·EtOH, such as crystalline form 1 of 4-glutarato-N,N-DiPT·EtOH, and an excipient (e.g., a pharmaceutically-acceptable excipient). In another embodiment, the disclosure also relates to pharmaceutical compositions comprising a therapeutically effective amount of 4-glutarato-N,N-DiPT·EtOH or crystalline 4-glutarato-N,N-DiPT·EtOH, such as crystalline form 1 of 4-glutarato-N,N-DiPT·EtOH, and a pharmaceutically acceptable excipient (also known as a pharmaceutically acceptable carrier). As discussed above, 4-glutarato-N,N-DiPT·EtOH or crystalline 4-glutarato-N,N-DiPT·EtOH, such as crystalline form 1 of 4-glutarato-N,N-DiPT·EtOH, of the disclosure may be, for example, therapeutically useful to prevent and/or treat the psychological disorders, brain disorders, pain, and inflammation as well as the other disorders described herein.

A composition or a pharmaceutical composition of the disclosure may be in any form which contains 4-glutarato-N,N-DiPT·EtOH or crystalline 4-glutarato-N,N-DiPT·EtOH, such as crystalline form 1 of 4-glutarato-N,N-DiPT·EtOH. The composition may be, for example, a tablet, capsule, liquid suspension, injectable, topical, or transdermal. The compositions generally contain, for example, about 1% to about 99% by weight of 4-glutarato-N,N-DiPT·EtOH or crystalline 4-glutarato-N,N-DiPT·EtOH, such as crystalline form 1 of 4-glutarato-N,N-DiPT·EtOH, of the disclosure and, for example, 99% to 1% by weight of at least one suitable pharmaceutically acceptable excipient. In one embodiment, the composition may be between about 5% and about 75% by weight of 4-glutarato-N,N-DiPT·EtOH or crystalline 4-glutarato-N,N-DiPT·EtOH, such as crystalline form 1 of 4-glutarato-N,N-DiPT·EtOH, of the disclosure, with the rest being at least one suitable pharmaceutically acceptable excipient or at least one other adjuvant, as discussed below.

According to this disclosure, 4-glutarato-N,N-DiPT·EtOH or crystalline 4-glutarato-N,N-DiPT·EtOH, such as crystalline form 1 of 4-glutarato-N,N-DiPT·EtOH, of the disclosure may be used as the "first purified psilocybin derivative" in the compositions described in US 2018/0221396 A1 and US 2019/0142851 A1. Accordingly, this disclosure provides a composition comprising: a first component comprising 4-glutarato-N,N-DiPT·EtOH or crystalline 4-glutarato-N,N-DiPT·EtOH, such as crystalline form 1 of 4-glutarato-N,N-DiPT·EtOH, of the disclosure; at least one second component selected from at least one of (a) a serotonergic drug, (b) a purified psilocybin derivative, (c) a purified cannabinoid, and (d) a purified terpene; and at least one pharmaceutically-acceptable excipient or at least one other adjuvant. Such a composition may be a pharmaceutical composition wherein the components are present individually in therapeutically effective amounts or by combination in a therapeutically effective amount to treat a disease, disorder, or condition as described herein.

When used in such compositions as a first component comprising 4-glutarato-N,N-DiPT·EtOH or crystalline 4-glutarato-N,N-DiPT·EtOH, such as crystalline form 1 of 4-glutarato-N,N-DiPT·EtOH, of the disclosure with a second component selected from at least one of (a) a serotonergic drug, (b) a purified psilocybin derivative, (c) a purified cannabinoid, and (d) a purified terpene, the compositions represent particular embodiments of the invention. Compositions having as a first component 4-glutarato-N,N-DiPT·EtOH or crystalline 4-glutarato-N,N-DiPT·EtOH, such as crystalline form 1 of 4-glutarato-N,N-DiPT·EtOH, of the disclosure with a second component selected from at least one of (e) an adrenergic drug, (f) a dopaminergic drug, (g) a monoamine oxidase inhibitor, (h) a purified erinacine, and (i) a purified hericenone represent additional particular embodiments of the invention represented by the compositions having 4-glutarato-N,N-DiPT·EtOH or crystalline 4-glutarato-N,N-DiPT·EtOH, such as crystalline form 1 of 4-glutarato-N,N-DiPT·EtOH, according to the disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

A pharmaceutical formulation of the disclosure may comprise, consist essentially of, or consist of (a) 4-glutarato-N,N-DiPT·EtOH or crystalline 4-glutarato-N,N-DiPT·EtOH, such as crystalline form 1 of 4-glutarato-N,N-DiPT·EtOH, of the disclosure and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone, and (c) a pharmaceutically acceptable excipient. In some embodiments, 4-glutarato-N,N-DiPT·EtOH or crystalline 4-glutarato-N,N-DiPT·EtOH, such as crystalline form 1 of 4-glutarato-N,N-DiPT·EtOH, and the second active compound(s) are each present in a therapeutically effective amount using purposefully engineered and unnaturally occurring molar ratios. Exemplary molar ratios of 4-glutarato-N,N-DiPT·EtOH or crystalline 4-glutarato-N,N-DiPT·EtOH, such as crystalline form 1 of 4-glutarato-N,N-DiPT·EtOH, of the disclosure to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing 4-glutarato-N,N-DiPT·EtOH or crystalline 4-glutarato-N,N-DiPT·EtOH, such as crystalline form 1 of 4-glutarato-N,N-DiPT·EtOH, of the disclosure and a serotonergic drug, a purified psilocybin derivative, a purified cannabinoid, or a purified terpene, each present in a therapeutically effective amount using purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. According to this disclosure composition containing 4-glutarato-N,N-DiPT·EtOH or crystalline 4-glutarato-N,N-DiPT·EtOH, such as crystalline form 1 of 4-glutarato-N,N-DiPT·EtOH, of the disclosure may be used in place of a "purified psilocybin derivative" in the compositions described in US 2018/0221396 A1 and US 2019/0142851 A1. Accordingly, the disclosure provides a pharmaceutical formulation comprising as (a) 4-glutarato-N,N-DiPT·EtOH or crystalline 4-glutarato-N,N-DiPT·EtOH, such as crystalline form 1 of 4-glutarato-N,N-DiPT·EtOH, of the disclosure and at least one second component selected from (a) a purified psilocybin derivative, (b) a purified cannabinoid, and (c) a purified terpene; and at least one pharmaceutically-acceptable excipient or at least one other adjuvant, as described herein. Such a composition may be a pharmaceutical composition wherein the components are present individually in therapeutically effective amounts or by combination in a therapeutically effective amount to treat a disease, disorder, or condition as described herein.

For the purposes of this disclosure, exemplary serotonergic drugs, psilocybin derivatives, cannabinoids, terpenes, adrenergic drugs, dopaminergic drugs, monoamine oxidase inhibitors, erinacines, and hericenones are disclosed above.

Exemplary compositions of 4-glutarato-N,N-DiPT·EtOH or crystalline 4-glutarato-N,N-DiPT·EtOH, such as crystalline form 1 of 4-glutarato-N,N-DiPT·EtOH, of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone in exemplary molar ratios are shown in Table 3. 4-glutarato-N,N-DiPT·EtOH or crystalline 4-glutarato-N,N-DiPT·EtOH, such as crystalline form 1 of 4-glutarato-N,N-DiPT·EtOH, of the disclosure may be any one of the exemplary embodiments described above including the crystalline forms as disclosed herein.

TABLE 3

| Second Compound | Molar ratio of 4-glutarato-N,N-DiPT•EtOH or crystalline 4-glutarato-N,N-DiPT•EtOH, such as crystalline form 1 of 4-glutarato-N,N-DiPT•EtOH: second compound | Molar ratio of 4-glutarato-N,N-DiPT•EtOH or crystalline 4-glutarato-N,N-DiPT•EtOH, such as crystalline form 1 of 4-glutarato-N,N-DiPT•EtOH: second compound | Molar ratio of a 4-glutarato-N,N-DiPT•EtOH or crystalline 4-glutarato-N,N-DiPT•EtOH, such as crystalline form 1 of 4-glutarato-N,N-DiPT•EtOH: second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| Duloxetine | About 1:100 to about 100:1 | About 1:25 to about 25:1 | About 1:5 to about 5:1 |
| [3-(2-dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

Exemplary pharmaceutical compositions of 4-glutarato-N,N-DiPT·EtOH or crystalline 4-glutarato-N,N-DiPT·EtOH, such as crystalline form 1 of 4-glutarato-N,N-DiPT·EtOH, of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone and an excipient with exemplary molar ratios of 4-glutarato-N,N-DiPT·EtOH or crystalline 4-glutarato-N,N-DiPT·EtOH, such as crystalline form 1 of 4-glutarato-N,N-DiPT·EtOH, to the second compound are shown in Table 4. 4-glutarato-N,N-DiPT·EtOH or crystalline 4-glutarato-N,N-DiPT·EtOH, such as crystalline form 1 of 4-glutarato-N,N-DiPT·EtOH, of the disclosure may be any one of the exemplary embodiments described above including the crystalline forms as disclosed herein.

TABLE 4

| Second Compound | Molar ratio of a 4-glutarato-N,N-DiPT•EtOH or crystalline 4-glutarato-N,N-DiPT•EtOH, such as crystalline form 1 of 4-glutarato-N,N-DiPT•EtOH: second compound | Molar ratio of a 4-glutarato-N,N-DiPT•EtOH or crystalline 4-glutarato-N,N-DiPT•EtOH, such as crystalline form 1 of 4-glutarato-N,N-DiPT•EtOH: second compound | Molar ratio of a 4-glutarato-N,N-DiPT•EtOH or crystalline 4-glutarato-N,N-DiPT•EtOH, such as crystalline form 1 of 4-glutarato-N,N-DiPT•EtOH: second compound |
|---|---|---|---|
| 3,4-methylenedioxy-methamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| Duloxetine | About 1:100 to about 100:1 | About 1:25 to about 25:1 | About 1:5 to about 5:1 |
| [3-(2-dimethylaminoethyl)-1H-indol-4-yl] dihydrogen phosphate | About 1:100 to about 100:1 | About 1:25 to about 25:1 | About 1:5 to about 5:1 |
| 4-hydroxy-tryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

An "effective amount" or a "therapeutically effective amount" of 4-glutarato-N,N-DiPT·EtOH or crystalline 4-glutarato-N,N-DiPT·EtOH, such as crystalline form 1 of 4-glutarato-N,N-DiPT·EtOH, of the disclosure is generally in the range of about 0.1 to about 100 mg daily (oral dose), of about 0.1 to about 50 mg daily (oral dose), of about 0.25 to about 25 mg daily (oral dose), of about 0.1 to about 5 mg daily (oral dose), or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. 4-glutarato-N,N-DiPT·EtOH or crystalline 4-glutarato-N,N-DiPT·EtOH, such as crystalline form 1 of 4-glutarato-N,N-DiPT·EtOH, of the disclosure and pharmaceutical compositions containing it may be used in combination with other agents that are generally administered to a patient being treated for psychological and other disorders discussed above. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Exemplary carriers include those that do not substantially alter the structure or activity of 4-glutarato-N,N-DiPT·EtOH or crystalline 4-glutarato-N,N-DiPT·EtOH, such as crystalline form 1 of 4-glutarato-N,N-DiPT·EtOH, of the disclosure, or produce undesirable biological effects or otherwise interact in a deleterious manner with any other component(s) of the pharmaceutical composition.

The pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, 4-glutarato-N,N-DiPT·EtOH or crystalline 4-glutarato-N,N-DiPT·EtOH, such as crystalline form 1 of 4-glutarato-N,N-DiPT·EtOH, of the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. In some embodiments, the excipient is not water. In some embodiments, the excipient is not a solvent (e.g., EtOH, diethyl ether, ethyl acetate, or hydrocarbon-based solvents (e.g., hexanes). In some embodiments, the dosage form is substantially free of water and/or solvents, for example less than about 5% water by mass, less than 2% water by mass, less than 1% water by mass, less than 0.5% water by mass, or less than 0.1% water by mass.

For purposes of this disclosure, excipients or pharmaceutically acceptable adjuvants, solid dosage forms, suspensions, and solid dosage forms for oral administration are disclosed above.

Administration of 4-glutarato-N,N-DiPT·EtOH or crystalline 4-glutarato-N,N-DiPT·EtOH, such as crystalline form 1 of 4-glutarato-N,N-DiPT·EtOH, of the disclosure in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

The disclosure also relates to compositions comprising an effective amount of crystalline baeocystin, such as crystalline form 1 of baeocystin, including its exemplary embodiments discussed above, and an excipient (e.g., a pharmaceutically-acceptable excipient). In another embodiment, the disclosure also relates to pharmaceutical compositions comprising a therapeutically effective amount of crystalline baeocystin, such as crystalline form 1 of baeocystin, including its exemplary embodiments discussed above, and a pharmaceutically acceptable excipient (also known as a pharmaceutically acceptable carrier). As discussed above, a crystalline baeocystin of the disclosure, such as crystalline form 1 of baeocystin, may be, for example, therapeutically useful to prevent and/or treat the psychological disorders, brain disorders, pain, and inflammation as well as the other disorders described herein.

A composition or a pharmaceutical composition of the disclosure may be in any form which contains crystalline baeocystin, such as crystalline form 1 of baeocystin. The composition may be, for example, a tablet, capsule, liquid suspension, injectable, topical, or transdermal. The compositions generally contain, for example, about 1% to about 99% by weight of crystalline baeocystin, such as crystalline form 1 of baeocystin, and, for example, 99% to 1% by weight of at least one suitable pharmaceutically acceptable excipient. In one embodiment, the composition may be between about 5% and about 75% by weight of crystalline baeocystin, such as crystalline form 1 of baeocystin, with the rest being at least one suitable pharmaceutically acceptable excipient or at least one other adjuvant, as discussed below.

According to this disclosure, crystalline baeocystin according to this disclosure, such as crystalline form 1 of baeocystin, may be used as the "first purified psilocybin derivative" in the compositions described in US 2018/0221396 A1 and US 2019/0142851 A1. Accordingly, this disclosure provides a composition comprising: a first component comprising crystalline baeocystin according to the disclosure, such as crystalline form 1 of baeocystin; at least one second component selected from at least one of (a) a serotonergic drug, (b) a purified psilocybin derivative, (c) a purified cannabinoid or (d) a purified terpene; and at least one pharmaceutically-acceptable excipient or at least one other adjuvant. Such a composition may be a pharmaceutical composition wherein the components are present individually in therapeutically effective amounts or by combination in a therapeutically effective amount to treat a disease, disorder, or condition as described herein.

When used in such compositions as a first component comprising crystalline baeocystin according to this disclosure, such as crystalline form 1 of baeocystin, with a second component selected from at least one of (a) a serotonergic drug, (b) a purified psilocybin derivative, (c) a purified cannabinoid, or (d) a purified terpene, the compositions represent particular embodiments of the invention. Compositions having as a first component at least crystalline baeocystin of the disclosure, such as crystalline form 1 of baeocystin, with a second component selected from at least one of (e) an adrenergic drug, (f) a dopaminergic drug, (g) a monoamine oxidase inhibitor, (h) a purified erinacine, (i)

a purified hericenone represent additional particular embodiments of the invention represented by the compositions having crystalline baeocystin according to the disclosure, such as crystalline form 1 of baeocystin. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

A pharmaceutical formulation of the disclosure may comprise, consist essentially of, or consist of (a) crystalline baeocystin according to this disclosure, such as crystalline form 1 of baeocystin, and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and (c) a pharmaceutically acceptable excipient. In some embodiments, crystalline baeocystin, such as crystalline form 1 of baeocystin, and the second active compound(s) are each present in a therapeutically effective amount using a purposefully engineered and unnaturally occurring molar ratios. Exemplary molar ratios of crystalline baeocystin according to the disclosure, such as crystalline form 1 of baeocystin, to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing crystalline baeocystin according to this disclosure, such as crystalline form 1 of baeocystin, and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. According to this disclosure a composition containing crystalline baeocystin according to the disclosure, such as crystalline form 1 of baeocystin, may be used in place of a "purified psilocybin derivative" in the compositions described in US 2018/0221396 A1 and US 2019/0142851 A1. Accordingly, the disclosure provides a pharmaceutical formulation comprising as (a) at least one of a crystalline baeocystin according to the disclosure, such as crystalline form 1 of baeocystin, and at least one second component selected from (a) a purified psilocybin derivative, (b) a purified cannabinoid or (c) a purified terpene; and at least one pharmaceutically-acceptable excipient or at least one other adjuvant, as described herein. Such a composition may be a pharmaceutical composition wherein the components are present individually in therapeutically effective amounts or by combination in a therapeutically effective amount to treat a disease, disorder, or condition as described herein.

For the purposes of this disclosure, exemplary serotonergic drugs, psilocybin derivatives, cannabinoids, terpenes, adrenergic drugs, dopaminergic drugs, monoamine oxidase inhibitors, erinacines, and hericenones are disclosed above.

Exemplary compositions of crystalline baeocystin according to the disclosure, such as crystalline form 1 of baeocystin, and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone in exemplary molar ratios are shown in Table 5. Crystalline baeocystin according to the disclosure, such as crystalline form 1 of baeocystin, may be any one of the exemplary embodiments described above including the crystalline form of those compounds as disclosed herein.

TABLE 5

| Second Compound | Molar ratio of crystalline baeocystin, such as crystalline form 1 of baeocystin: second compound | Molar ratio of crystalline baeocystin, such as crystalline form 1 of baeocystin: second compound | Molar ratio of crystalline baeocystin, such as crystalline form 1 of baeocystin: second compound |
|---|---|---|---|
| 3,4-methylenedioxy-methamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| Duloxetine | About 1:100 to about 100:1 | About 1:25 to about 25:1 | About 1:5 to about 5:1 |
| [3-(2-dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methyl-aminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethyl-aminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |

TABLE 5-continued

| Second Compound | Molar ratio of crystalline baeocystin, such as crystalline form 1 of baeocystin: second compound | Molar ratio of crystalline baeocystin, such as crystalline form 1 of baeocystin: second compound | Molar ratio of crystalline baeocystin, such as crystalline form 1 of baeocystin: second compound |
| --- | --- | --- | --- |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

Exemplary pharmaceutical compositions of crystalline baeocystin according to the disclosure, such as crystalline form 1 of baeocystin, and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and an excipient with exemplary molar ratios of crystalline baeocystin, such as crystalline form 1 of baeocystin, according to the second compound are shown in Table 6. Crystalline baeocystin according to the disclosure, such as crystalline form 1 of baeocystin, may be any one of the exemplary embodiments described above including the crystalline form as disclosed herein.

TABLE 6

| Second Compound | Molar ratio of crystalline baeocystin, such as crystalline form 1 of baeocystin: second compound | Molar ratio of crystalline baeocystin, such as crystalline form 1 of baeocystin: second compound | Molar ratio of crystalline baeocystin, such as crystalline form 1 of baeocystin: second compound |
| --- | --- | --- | --- |
| 3,4-methylenedioxy-methamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| Duloxetine | About 1:100 to about 100:1 | About 1:25 to about 25:1 | About 1:5 to about 5:1 |
| [3-(2-dimethyl-aminoethyl)-1H-indol-4-yl] dihydrogen phosphate 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |

TABLE 6-continued

| Second Compound | Molar ratio of crystalline baeocystin, such as crystalline form 1 of baeocystin: second compound | Molar ratio of crystalline baeocystin, such as crystalline form 1 of baeocystin: second compound | Molar ratio of crystalline baeocystin, such as crystalline form 1 of baeocystin: second compound |
| --- | --- | --- | --- |
| [3-(2-methyl-aminoethyl)-1H-indol-4-yl] dihydrogen phosphate 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethyl-aminoethyl)-1H-indol-4-yl] dihydrogen phosphate 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

An "effective amount" or a "therapeutically effective amount" of crystalline baeocystin according to the disclosure, such as crystalline form 1 of baeocystin, is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. Crystalline baeocystin of the disclosure, such as crystalline form 1 of baeocystin, and pharmaceutical compositions containing it may be used in combination with other agents that are generally administered to a patient being treated for psychological and other disorders discussed above. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Exemplary carriers include those that do not substantially alter the structure or activity of crystalline baeocystin according to the disclosure, such as crystalline form 1 of baeocystin, or produce undesirable biological effects or otherwise interact in a deleterious manner with any other component(s) of the pharmaceutical composition.

The pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, crystalline baeocystin of the disclosure, such as crystalline form 1 of baeocystin, may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. In some embodiments, the excipient is not water. In some embodiments, the excipient is not a solvent (e.g., EtOH, diethyl ether, ethyl acetate, or hydrocarbon-based solvents (e.g., hexanes). In some embodiments, the dosage form is substantially free of water and/or solvents, for example less than about 5% water by mass, less than 2% water by mass, less than 1% water by mass, less than 0.5% water by mass, or less than 0.1% water by mass.

For purposes of this disclosure, excipients or pharmaceutically acceptable adjuvants, solid dosage forms, suspensions, and solid dosage forms for oral administration are disclosed above.

Administration of crystalline baeocystin according to the disclosure, such as crystalline form 1 of baeocystin, in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

Single Crystal X-Ray Diffraction (SCXRD) Characterization: Data were collected on a Bruker APEX-II CCD Diffractometer equipped with an Oxford Cryosystems Cryostream cooling device and using Mo Kα radiation. Structures were solved using the Bruker SHELXTL program and refined with the SHELXTL program as part of the Bruker SHELXTL suite, or OLEX2 software. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Example 1: Preparation of 5-[(3-{2-[bis(propan-2-yl)azaniumyl]ethyl}-1H-indol-4-yl)oxy]-5-oxopentanoate solvates Solvates of 5-[(3-{2-[bis(propan-2-yl)azaniumyl]ethyl}-1H-indol-4-yl)oxy]-5-oxopentanoate can be prepared by dissolving 4-hydroxy-N,N-diisopropyltryptamine freebase in chloroform and combining with triethylamine and glutaric anhydride. A precipitate can be produced by stirring the mixture at ambient temperature for 30 minutes. The precipitate can be isolated via filtration, triturating with tetrahydrofuran, filtering, and washing with chloroform. To obtain single crystals suitable for X-ray diffraction the powder can be recrystallized from a solvent. The solvent may be selected, for example, from the compounds in Table 7.

TABLE 7

| Solvent |
| --- |
| Ethanol |
| Propanol |
| Isopropanol |
| Water |
| Dimethyl ether |
| Diethyl ether |
| Fumaric acid |
| Maleic acid |
| Oxalic acid |
| Succinic acid |
| Glutaric acid |
| Acetic acid |

Example 2: Preparation and Characterization of Crystalline Form 1 of methanol 5-[(3-{2-[bis(propan-2-yl)azaniumyl]ethyl}-1H-indol-4-yl)oxy]-5-oxopentanoate The preparation and characterization of crystalline form 1 of methanol 5-[(3-{2-[bis(propan-2-yl)azaniumyl]ethyl}-

1H-indol-4-yl)oxy]-5-oxopentanoate (4-glutarato-N,N-diisopropyltryptamine methanol solvate or 4-glutarato-DiPT·MeOH) are described below.

Preparation 112 mg of 4-hydroxy-N,N-diisopropyltryptamine freebase was dissolved in 5 mL of chloroform and combined with 0.3 mL of triethylamine and 490 mg of glutaric anhydride. The mixture was stirred at ambient temperature for 30 minutes producing a precipitate. The precipitate was isolated via filtration, was triturated with tetrahydrofuran, filtered, and washed with chloroform to obtain a white powder (73 mg, 65% yield). The powder was recrystallized from boiling methanol to yield single crystals suitable for X-ray diffraction.

Single Crystal Characterization

The single crystal data and structure refinement parameters for the crystalline form 1 structure of 4-glutarato-DiPT·MeOH measured at 297 K are reported in Table 8, below.

TABLE 8

| Crystal data | |
|---|---|
| Chemical formula | $C_{21}H_{30}N_2O_4$·$CH_4O$ |
| $M_r$ | 406.51 |
| Crystal system, space group | Monoclinic, $P2_1/c$ |
| Temperature (K) | 297 |
| a, b, c (Å) | 7.9531 (5), 13.4224 (7), 21.2015 (11) |
| β (°) | 92.484 (2) |
| θ (°) | 2.98-25.58 |
| V (Å$^3$) | 2261.1 (2) |
| Z | 4 |
| F (000) | 880 |
| $D_x$ (Mg m$^{-3}$) | 1.194 |
| Radiation type | Mo Kα |
| λ (Å) | 0.71073 |
| μ (mm$^{-1}$) | 0.084 |
| Crystal color | Colourless |
| Crystal description | Block |
| Crystal size (mm) | 0.22 × 0.21 × 0.2 |
| Data collection | |
| Diffractometer | Bruker APEX-II photon |
| Absorption correction | Multi-scan SADABS2016/2 (Bruker, 2016/2) was used for absorption correction. wR2(int) was 0.0551 before and 0.0492 after correction. The Ratio of minimum to maximum transmission is 0.9631. The λ/2 correction factor is not present. |
| $T_{min}$, $T_{max}$ | 0.7178, 0.7453 |
| No. of measured, independent, and observed [I > 2σ(I)] reflections | 61210, 4304, 3531 |
| $R_{int}$ | 0.0386 |
| $θ_{max}$, $θ_{min}$ (°) | 25.705, 2.979 |
| h | −9→9 |
| k | −16→16 |
| l | −25→25 |
| Refinement | |
| R[F$^2$ > 2σ(F$^2$)], wR(F$^2$), S | 0.0498, 0.1433, 1.034 |
| No. of reflections | 4304 |
| No. of parameters | 279 |
| No. of restraints | 3 |
| Hydrogen site location | mixed |
| H-atom treatment | H atoms treated by a mixture of independent and constrained refinement |
| w | $1/[σ^2(F_o^2) + (0.0677P)^2 + 1.0658P]$ where $P = (F_o^2 + 2F_c^2)/3$ |

TABLE 8-continued

| | |
|---|---|
| $(Δ/σ)_{max}$ | <0.001 |
| $Δρ_{max}$, $Δρ_{min}$ (e Å$^{-3}$) | 0.463, −0.393 |
| Extinction Correction: SHELXL2018/3 (Sheldrick 2018) | $Fc^* = kFc[1 + 0.001×Fc^2λ^3/\sin(2θ)]^{-1/4}$ |
| Extinction Coefficient | 0.0049 (16) |

Data collection: Bruker APEX4; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

FIG. 1 shows the molecular structure of crystalline form 1 of 4-glutarato-DiPT·MeOH with atomic labeling. Displacement ellipsoids are drawn at 50% probability level. Hydrogen bonds are shown as dashed lines.

Figure 2:
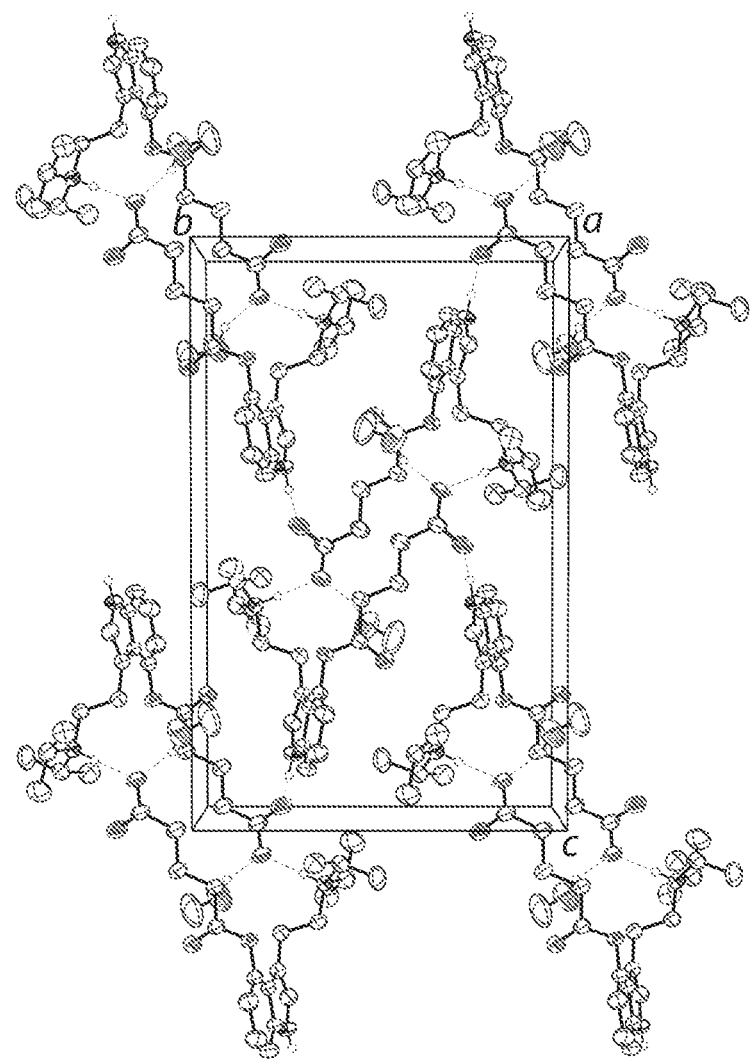
FIG. 2 shows the unit cell crystal packing of crystalline form 1 of 4-glutarato-DiPT·MeOH viewed along the a-axis; hydrogen bonds are shown as dashed lines.

FIG. 2 shows the unit cell crystal packing of crystalline form 1 of 4-glutarato-DiPT·MeOH, viewed along the a-axis. The N-H···O and O-H···O hydrogen bonds are shown as dashed lines. Displacement ellipsoids are drawn at the 50% probability level.

Simulated X-ray Powder Diffraction (XRPD) Pattern

Figure 3:
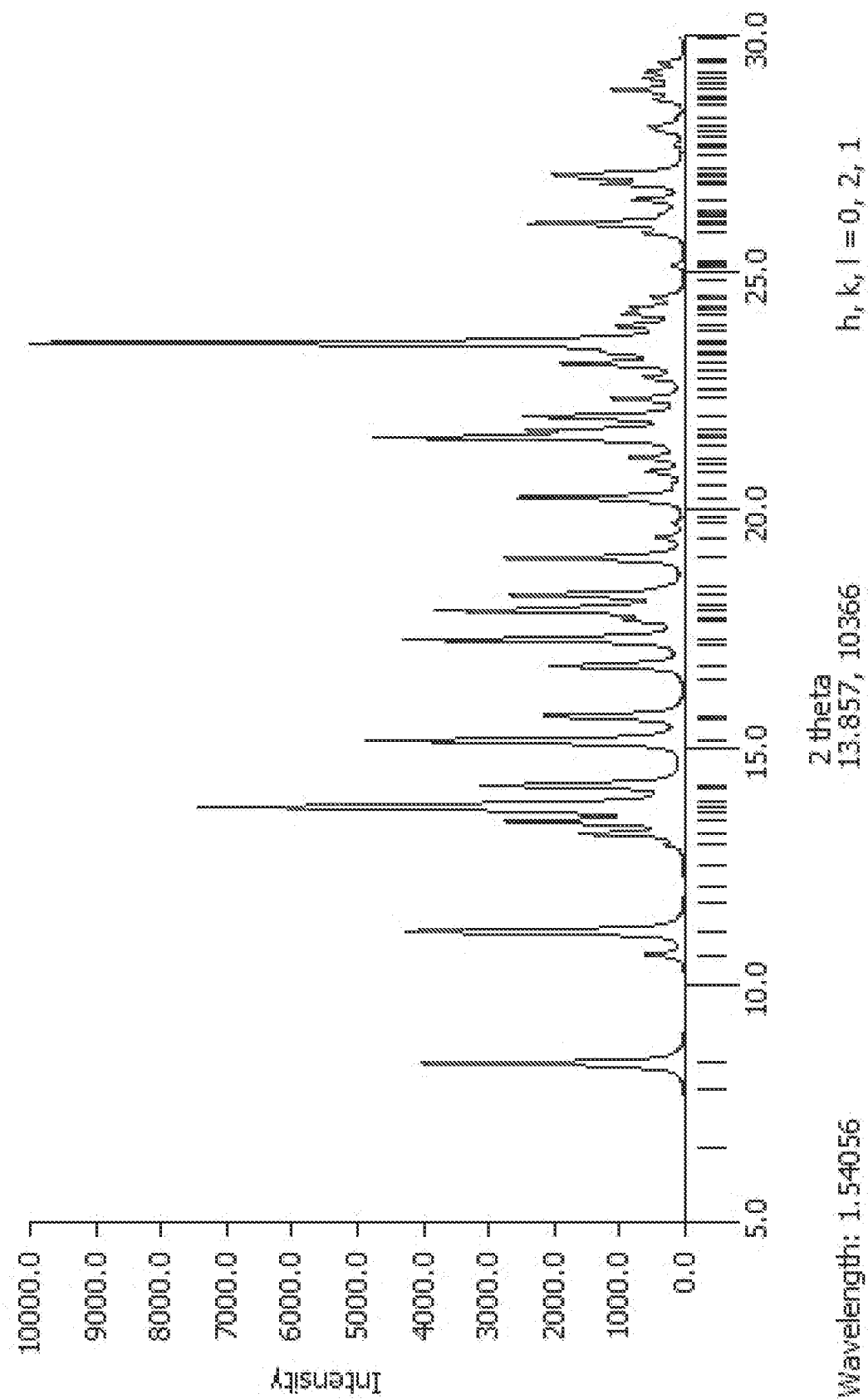
FIG. 3 shows a simulated X-ray powder diffraction pattern (XRPD) for crystalline form 1 of 4-glutarato-DiPT·MeOH generated from its single crystal data.

FIG. 3 shows a simulated X-ray powder diffraction pattern (XRPD) for crystalline form 1 of 4-glutarato-DiPT·MeOH generated from its single crystal data. Table 9 lists the angles, °2θ±0.2°2θ, and d-spacing of the peaks identified in the experimental XRPD pattern of FIG. 3. The entire list of peaks, or a subset thereof, may be sufficient to characterize the cocrystal. For example, the cocrystal may be characterized by at least two peaks selected from the peaks at 8.3, 11.1, and 15.1°2θ±0.2°2θ or their corresponding d-spacing as well as by a XRPD pattern substantially similar to FIG. 3.

TABLE 9

| d-spacing (Å) | °2θ ± 0.2°2θ | Intensity |
|---|---|---|
| 11.34 | 7.8 | 37 |
| 10.59 | 8.3 | 9114 |
| 8.31 | 10.6 | 2202 |
| 7.95 | 11.1 | 17570 |
| 6.84 | 12.9 | 1190 |
| 6.71 | 13.2 | 8571 |
| 6.58 | 13.4 | 15252 |
| 6.49 | 13.6 | 3692 |
| 6.44 | 13.7 | 43568 |
| 6.40 | 13.8 | 10548 |
| 6.25 | 14.2 | 312 |
| 6.23 | 14.2 | 20727 |
| 5.84 | 15.1 | 37399 |
| 5.67 | 15.6 | 3691 |
| 5.65 | 15.7 | 15916 |
| 5.30 | 16.7 | 19421 |
| 5.13 | 17.3 | 42478 |
| 5.02 | 17.7 | 1494 |
| 5.01 | 17.7 | 6110 |
| 4.95 | 17.9 | 38440 |
| 4.93 | 18.0 | 6077 |
| 4.86 | 18.2 | 28635 |
| 4.82 | 18.4 | 1582 |
| 4.67 | 19.0 | 33231 |
| 4.56 | 19.4 | 5240 |
| 4.50 | 19.7 | 1933 |
| 4.38 | 20.3 | 36038 |
| 4.32 | 20.5 | 1505 |
| 4.26 | 20.8 | 8162 |
| 4.20 | 21.1 | 11857 |
| 4.16 | 21.4 | 694 |
| 4.12 | 21.5 | 71807 |
| 4.11 | 21.6 | 27 |

TABLE 9-continued

| d-spacing (Å) | °2θ ± 0.2°2θ | Intensity |
| --- | --- | --- |
| 4.09 | 21.7 | 30683 |
| 4.04 | 22.0 | 39075 |
| 3.97 | 22.4 | 18017 |
| 3.90 | 22.8 | 9525 |
| 3.85 | 23.1 | 32499 |
| 3.82 | 23.3 | 2602 |
| 3.81 | 23.3 | 11680 |
| 3.78 | 23.5 | 109053 |
| 3.78 | 23.5 | 85000 |
| 3.77 | 23.6 | 1073 |
| 3.74 | 23.8 | 836 |
| 3.72 | 23.9 | 16632 |
| 3.68 | 24.1 | 15734 |
| 3.67 | 24.2 | 7543 |
| 3.66 | 24.3 | 7191 |
| 3.63 | 24.5 | 833 |
| 3.63 | 24.5 | 1266 |
| 3.63 | 24.5 | 7146 |
| 3.58 | 24.8 | 11 |
| 3.54 | 25.1 | 191 |
| 3.54 | 25.1 | 3842 |
| 3.53 | 25.2 | 284 |
| 3.44 | 25.8 | 12457 |
| 3.42 | 26.0 | 49122 |
| 3.42 | 26.1 | 103 |
| 3.41 | 26.1 | 5357 |
| 3.41 | 26.1 | 3969 |
| 3.40 | 26.2 | 4410 |
| 3.38 | 26.3 | 2818 |
| 3.36 | 26.5 | 781 |
| 3.36 | 26.5 | 17394 |
| 3.31 | 26.9 | 27793 |
| 3.31 | 26.9 | 273 |
| 3.30 | 27.0 | 27455 |
| 3.29 | 27.1 | 35305 |
| 3.28 | 27.2 | 218 |
| 3.25 | 27.5 | 1048 |
| 3.22 | 27.7 | 467 |
| 3.22 | 27.7 | 3483 |
| 3.20 | 27.9 | 330 |
| 3.19 | 28.0 | 8356 |
| 3.18 | 28.1 | 10479 |
| 3.17 | 28.1 | 4048 |
| 3.16 | 28.3 | 2471 |
| 3.12 | 28.5 | 131 |
| 3.12 | 28.6 | 3 |
| 3.11 | 28.6 | 10097 |
| 3.11 | 28.7 | 3503 |
| 3.09 | 28.9 | 29364 |
| 3.09 | 28.9 | 2457 |
| 3.08 | 29.0 | 2582 |
| 3.07 | 29.1 | 15205 |
| 3.05 | 29.2 | 15499 |
| 3.03 | 29.4 | 9888 |
| 3.03 | 29.4 | 809 |
| 3.03 | 29.4 | 68 |
| 2.98 | 30.0 | 1200 |

Example 3: Preparation and Characterization of Crystalline Form 1 of ethanol 5-[(3-{2-[bis(propan-2-yl)azaniumyl]ethyl}-1H-indol-4-yl)oxy]-5-oxo-pentanoate (4-glutarato-N,N-diisopropyltryptamine ethanol solvate The preparation and characterization of crystalline form 1 of ethanol 5-[(3-{2-[bis(propan-2-yl)azaniumyl]ethyl}-1H-indol-4-yl)oxy]-5-oxopentanoate (4-glutarato-N,N-diisopropyltryptamine ethanol solvate or 4-glutarato-N,N-DiPT·EtOH) is described below.

Synthesis 112 mg of 4-hydroxy-N,N-diisopropyltryptamine freebase was dissolved in 5 mL of chloroform, and was combined with 0.3 mL of triethylamine and 490 mg of glutaric anhydride. The mixture was stirred at ambient temperature for 30 minutes producing a precipitate. The precipitate was isolated via filtration, was triturated with tetrahydrofuran, filtered and washed with chloroform to obtain a white powder (73 mg, 65% yield).

Preparation

Single crystals suitable for single crystal diffraction were grown from the slow evaporation of an ethanol solution.

Single Crystal Characterization

The single crystal data and structure refinement parameters for the crystalline form 1 structure of 4-glutarato-N,N-DiPT·EtOH are reported in Table 10, below.

TABLE 10

| Crystal data | |
| --- | --- |
| Chemical formula | $C_{21}H_{30}N_2O_4 \cdot C_2H_6O$ |
| $M_r$ | 420.54 |
| Crystal system, space group | monoclinic, $P2_{1/c}$ |
| Temperature (K) | 297(2) |
| a, b, c (Å) | 8.0087(12), 13.7968(17), 21.878(3) |
| α (°) | 90 |
| β (°) | 90.749(4) |
| γ (°) | 90 |
| V (Å$^3$) | 2417.2(5) |
| Z | 4 |
| F(000) | 912 |
| $D_x$ (Mg m$^{-3}$) | 1.156 |
| Radiation type | Mo Kα |
| λ (Å) | 0.71073 |
| θ (°) | 2.54-24.91 |
| μ (mm$^{-1}$) | 0.081 |
| Crystal size (mm) | 0.3 × 0.27 × 0.22 |
| Crystal color | colourless |
| Crystal description | BLOCK |
| Data collection | |
| Diffractometer | Bruker APEX-II CCD |
| Absorption correction | Multi-scan SADABS (Bruker, 2016) was used. wR2(int) was 0.0609 before and 0.0516 after correction. The Ratio of minimum to maximum transmission is 0.9287. The λ/2 correction factor is not present. |
| $T_{min}$, $T_{max}$ | 0.6921, 0.7452 |
| No. of measured, independent, and observed [[I > 2σ(I)] reflections | 33128, 3836, 2804 |
| $R_{int}$ | 0.0494 |
| $θ_{max}$, $θ_{min}$ (°) | 24.107, 2.543 |
| h, k, l | −9 → 9, −15 → 15, −25 → 25 |
| Refinement | |
| R[F$^2$ > 2σ(F$^2$)], wR(F$^2$), S | 0.0561, 0.1565, 1.05 |
| No. of reflections | 3836 |
| No. of parameters | 315 |
| No. of restraints | 47 |
| H-atom treatment | H atoms treated by a mixture of independent and constrained refinement |
| w | w = 1/[σ$^2$(F$_o^2$) + (0.0654P)$^2$ + 1.3596P] where P = (F$_o^2$ + 2F$_c^2$)/3 |
| (Δ/σ)$_{max}$ | <0.001 |
| Δρ$_{max}$, Δρ$_{min}$ (e Å$^{-3}$) | 0.350, −0.442 |

Data collection: Bruker APEX32; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

Figure 4:
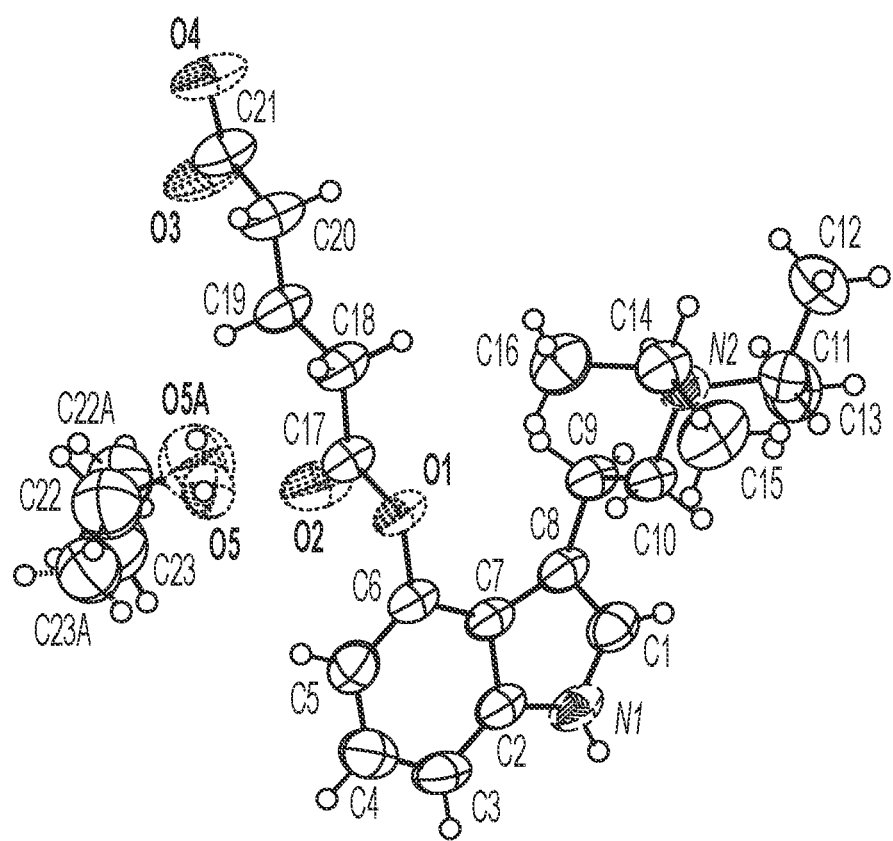
FIG. 4 shows the molecular structure of crystalline form 1 of 4-glutarato-N,N-diisopropyltryptamine ethanol solvate.

FIG. 4 shows the molecular structure of crystalline form 1 of 4-glutarato-N,N-DiPT·EtOH, showing the atomic labeling.

Figure 5:
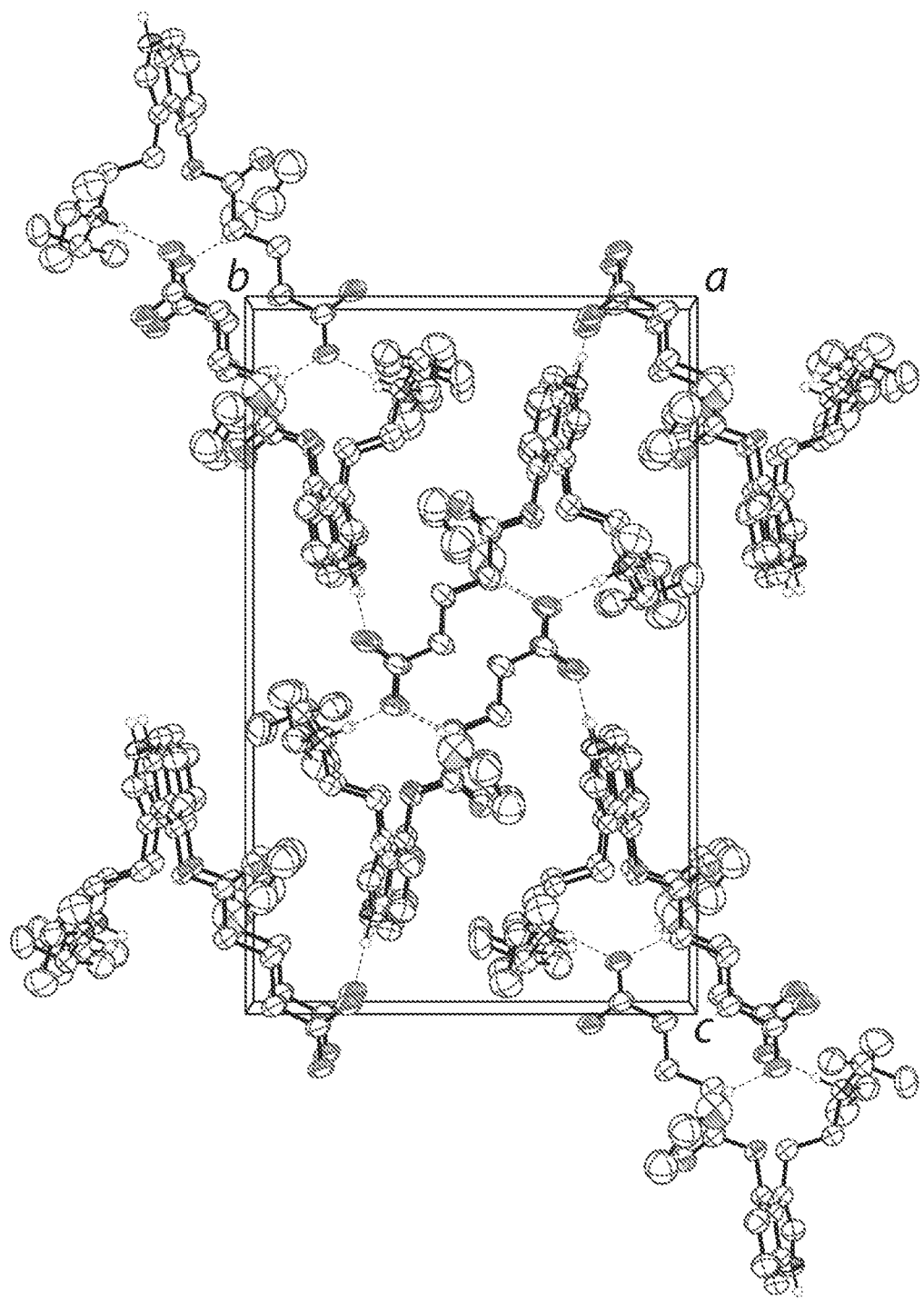
FIG. 5 shows the unit cell of crystalline form 1 of 4-glutarato-N,N-diisopropyltryptamine ethanol solvate along the a-axis.

FIG. 5 shows the unit cell of crystalline form 1 of 4-glutarato-N,N-DiPT·EtOH along the a-axis.

Simulated X-ray Powder Diffraction (XRPD) Pattern

Figure 6:
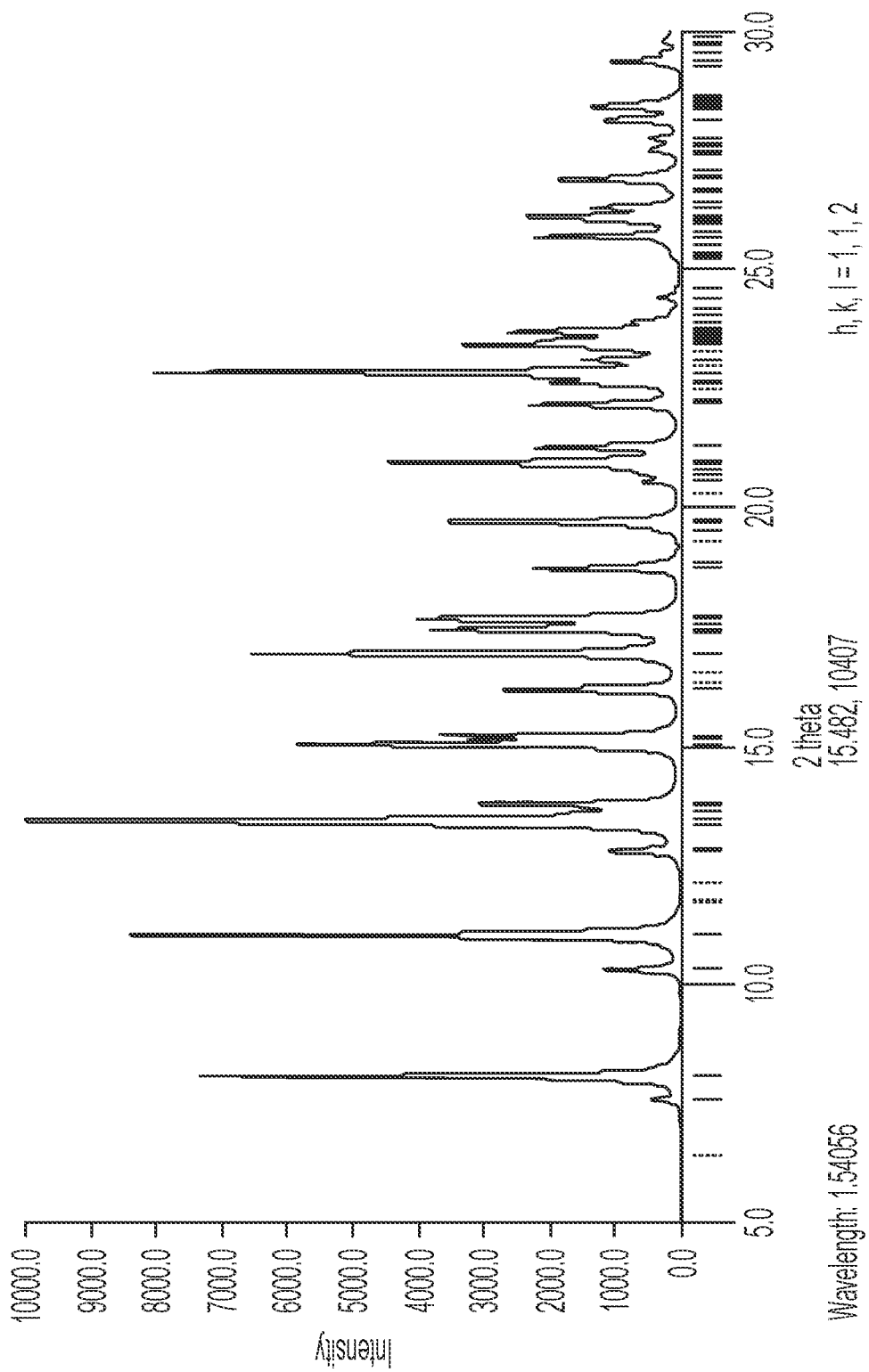
FIG. 6 shows the simulated X-ray powder diffraction pattern (XRPD) for crystalline form 1 of 4-glutarato-N,N-diisopropyltryptamine ethanol solvate.

FIG. 6 shows a simulated X-ray powder diffraction pattern (XRPD) for crystalline form 1 of 4-glutarato-N,N-DiPT·EtOH generated from its single crystal data. Table 11 lists the angles, °2θ±0.2°2θ, and d-spacing of the peaks identified in the experimental XRPD pattern of FIG. 6. The entire list of peaks, or a subset thereof, may be sufficient to characterize the cocrystal. For example, the cocrystal may be characterized by at least two peaks selected from the peaks at 8.1, 11.0, and 17.0° 2θ±0.2° 2θ or their corresponding d-spacing as well as by an XRPD pattern substantially similar to FIG. 6.

TABLE 11

| d-spacing (Å) | °2θ ± 0.2°2θ | Intensity |
| --- | --- | --- |
| 11.67 | 7.57 | 809 |
| 10.94 | 8.08 | 15050 |
| 8.57 | 10.31 | 4005 |
| 8.01 | 11.04 | 32136 |
| 6.93 | 12.77 | 2763 |
| 6.90 | 12.82 | 3943 |
| 6.62 | 13.35 | 13210 |
| 6.58 | 13.44 | 44384 |
| 6.58 | 13.45 | 9047 |
| 6.50 | 13.61 | 5046 |
| 6.45 | 13.72 | 57 |
| 6.42 | 13.78 | 16855 |
| 5.88 | 15.05 | 41061 |
| 5.83 | 15.17 | 1700 |
| 5.82 | 15.21 | 22568 |
| 5.47 | 16.19 | 22639 |
| 5.23 | 16.95 | 61350 |
| 5.09 | 17.40 | 658 |
| 5.08 | 17.43 | 15037 |
| 5.07 | 17.46 | 22498 |
| 5.05 | 17.55 | 7503 |
| 5.01 | 17.68 | 36960 |
| 4.99 | 17.75 | 2016 |
| 4.73 | 18.74 | 25144 |
| 4.70 | 18.86 | 1493 |
| 4.54 | 19.52 | 2849 |
| 4.50 | 19.71 | 44689 |
| 4.49 | 19.76 | 1384 |
| 4.32 | 20.56 | 6442 |
| 4.29 | 20.71 | 4789 |
| 4.27 | 20.79 | 1 |
| 4.27 | 20.81 | 5514 |
| 4.24 | 20.94 | 35205 |
| 4.23 | 20.98 | 37194 |
| 4.17 | 21.29 | 31262 |
| 4.00 | 22.18 | 36018 |
| 3.99 | 22.27 | 15 |
| 3.93 | 22.62 | 22363 |
| 3.92 | 22.67 | 9319 |
| 3.89 | 22.84 | 133638 |
| 3.85 | 23.11 | 20774 |
| 3.80 | 23.42 | 51161 |
| 3.79 | 23.42 | 1066 |
| 3.78 | 23.52 | 23526 |
| 3.78 | 23.54 | 1875 |
| 3.76 | 23.63 | 7 |
| 3.75 | 23.68 | 35258 |
| 3.74 | 23.74 | 19791 |
| 3.74 | 23.78 | 5017 |
| 3.72 | 23.91 | 10142 |
| 3.69 | 24.07 | 304 |
| 3.68 | 24.16 | 1223 |
| 3.65 | 24.39 | 807 |
| 3.64 | 24.42 | 5726 |
| 3.61 | 24.62 | 722 |
| 3.53 | 25.24 | 1217 |
| 3.52 | 25.28 | 769 |
| 3.51 | 25.36 | 2604 |
| 3.49 | 25.51 | 3198 |
| 3.46 | 25.70 | 47071 |
| 3.45 | 25.81 | 156 |
| 3.43 | 25.98 | 4440 |

TABLE 11-continued

| d-spacing (Å) | °2θ ± 0.2°2θ | Intensity |
| --- | --- | --- |
| 3.42 | 26.04 | 9442 |
| 3.41 | 26.08 | 10055 |
| 3.41 | 26.13 | 44973 |
| 3.38 | 26.32 | 27843 |
| 3.37 | 26.43 | 5 |
| 3.34 | 26.66 | 1231 |
| 3.33 | 26.71 | 1415 |
| 3.31 | 26.90 | 40779 |
| 3.30 | 26.98 | 12733 |
| 3.29 | 27.07 | 1161 |
| 3.29 | 27.08 | 364 |
| 3.25 | 27.41 | 352 |
| 3.24 | 27.49 | 9193 |
| 3.23 | 27.57 | 5239 |
| 3.22 | 27.65 | 1806 |
| 3.21 | 27.75 | 2346 |
| 3.21 | 27.76 | 1518 |
| 3.21 | 27.76 | 6924 |
| 3.17 | 28.13 | 0 |
| 3.17 | 28.15 | 28180 |
| 3.16 | 28.18 | 3356 |
| 3.14 | 28.38 | 884 |
| 3.14 | 28.42 | 32230 |
| 3.13 | 28.47 | 4282 |
| 3.13 | 28.52 | 6654 |
| 3.12 | 28.61 | 199 |
| 3.11 | 28.64 | 2370 |
| 3.05 | 29.28 | 60 |
| 3.05 | 29.29 | 292 |
| 3.04 | 29.37 | 32085 |
| 3.02 | 29.56 | 7077 |
| 3.00 | 29.73 | 2671 |
| 3.00 | 29.80 | 5994 |
| 2.99 | 29.88 | 3331 |
| 2.98 | 29.98 | 3574 |

Example 4: Preparation and Characterization of Crystalline Form 1 of [3-[2-(methylamino)ethyl]-1H-indol-4-yl] dihydrogen phosphate (Baeocystin The preparation and characterization of crystalline form 1 of [3-[2-(methylamino)ethyl]-1H-indol-4-yl] dihydrogen phosphate (baeocystin) are described below.

Preparation

Crystals suitable for X-ray diffraction were grown from the slow evaporation of an aqueous solution of a sample obtained from the National Institute of Health (NIH).

Single Crystal Characterization

The single crystal data and structure refinement parameters for the crystalline form 1 structure of baeocystin measured at 297 K are reported in Table 12, below.

TABLE 12

| Crystal data | |
| --- | --- |
| Chemical formula | $C_{11}H_{15}N_2O_4P$ |
| $M_r$ | 270.22 |
| Crystal system, space group | Orthorhombic, Pbca |
| Temperature (K) | 297 |
| a, b, c (Å) | 13.229 (1), 10.5551 (7), 17.8346 (13) |
| V (Å$^3$) | 2490.3 (3) |
| Z | 8 |
| F (000) | 1136 |
| $D_x$ (Mg m$^{-3}$) | 1.441 |
| Radiation type | Mo Kα |
| λ (Å) | 0.71073 |
| θ (°) | 2.7-26.2 |
| μ (mm$^{-1}$) | 0.23 |

TABLE 12-continued

| | |
|---|---|
| Crystal color | Colourless |
| Crystal description | Block |
| Crystal size (mm) | 0.25 × 0.2 × 0.03 |
| Data collection | |
| Diffractometer | Bruker APEX-II CCD |
| Absorption correction | Multi-scan SADABS2016/2 (Bruker, 2016/2) was used for absorption correction. wR2(int) was 0.0730 before and 0.0646 after correction. The Ratio of minimum to maximum transmission is 0.9120. The λ/2 correction factor is Not present. |
| $T_{min}$, $T_{max}$ | 0.680, 0.745 |
| No. of measured, independent and observed [I > 2σ(I)] reflections | 58953, 2551, 2155 |
| $R_{int}$ | 0.070 |
| $θ_{max}$, $θ_{min}$ (°) | 26.4, 2.8 |
| h | −16→16 |
| k | −13→13 |
| l | −22→22 |
| Refinement | |
| R[$F^2$ > 2σ($F^2$)], wR($F^2$), S | 0.037, 0.096, 1.07 |
| No. of reflections | 2551 |
| No. of parameters | 180 |
| No. of restraints | 4 |
| Hydrogen site location | mixed |
| H-atom treatment | H atoms treated by a mixture of independent and constrained refinement |
| w | $1/[σ^2(F_o^2) + (0.0425P)^2 + 1.441P]$ where P = $(F_o^2 + 2F_c^2)/3$ |
| $(Δ/σ)_{max}$ | 0.001 |
| $Δρ_{max}$, $Δρ_{min}$ (e Å$^{−3}$) | 0.21, −0.35 |
| Data collection: Bruker APEX3; cell refinement: Bruker SAINT; data reduction: Bruker SAINT; program(s) used to solve structure: SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009). | |

Figure 7:
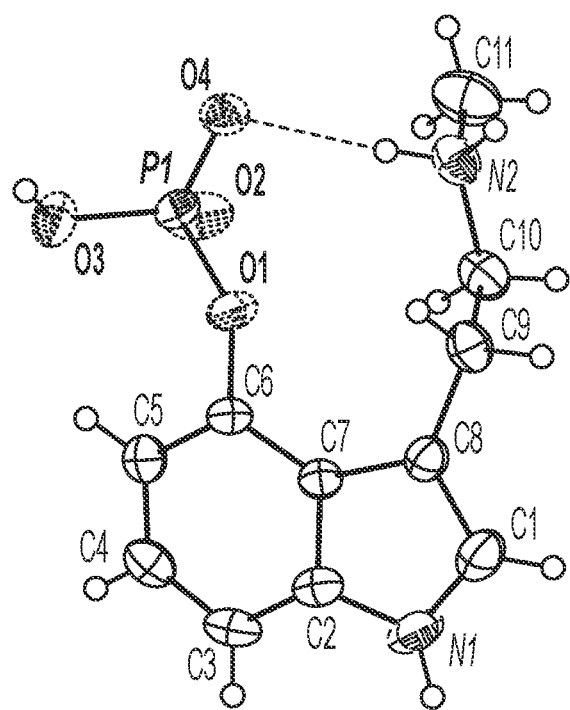
FIG. 7 shows the molecular structure of crystalline form 1 of baeocystin with atomic labeling; hydrogen bonds are shown as dashed lines.

FIG. 7 shows the molecular structure of crystalline form 1 of baeocystin with atomic labeling.

Displacement ellipsoids are drawn at 50% probability level. Hydrogen bonds are shown as dashed lines.

Figure 8:
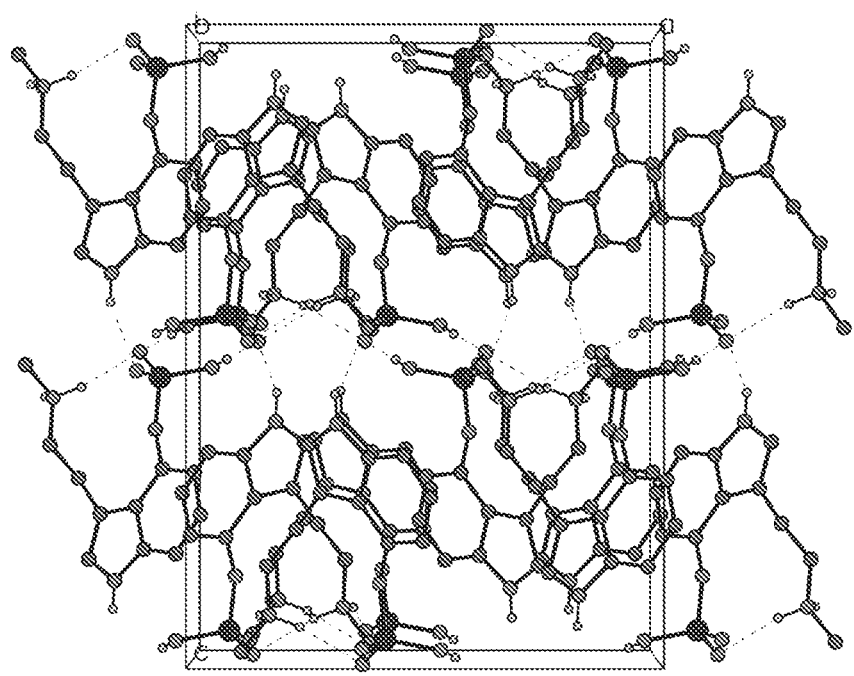
FIG. 8 shows the unit cell crystal packing of crystalline form 1 of baeocystin viewed along the b-axis; hydrogen bonds are shown as dashed lines.

FIG. 8 shows the unit cell crystal packing of crystalline form 1 of baeocystin, viewed along the b-axis. The N-H···O and O-H···O hydrogen bonds are shown as dashed lines. Displacement ellipsoids are drawn at the 50% probability level.

Simulated X-ray Powder Diffraction (XRPD) Pattern

Figure 9:
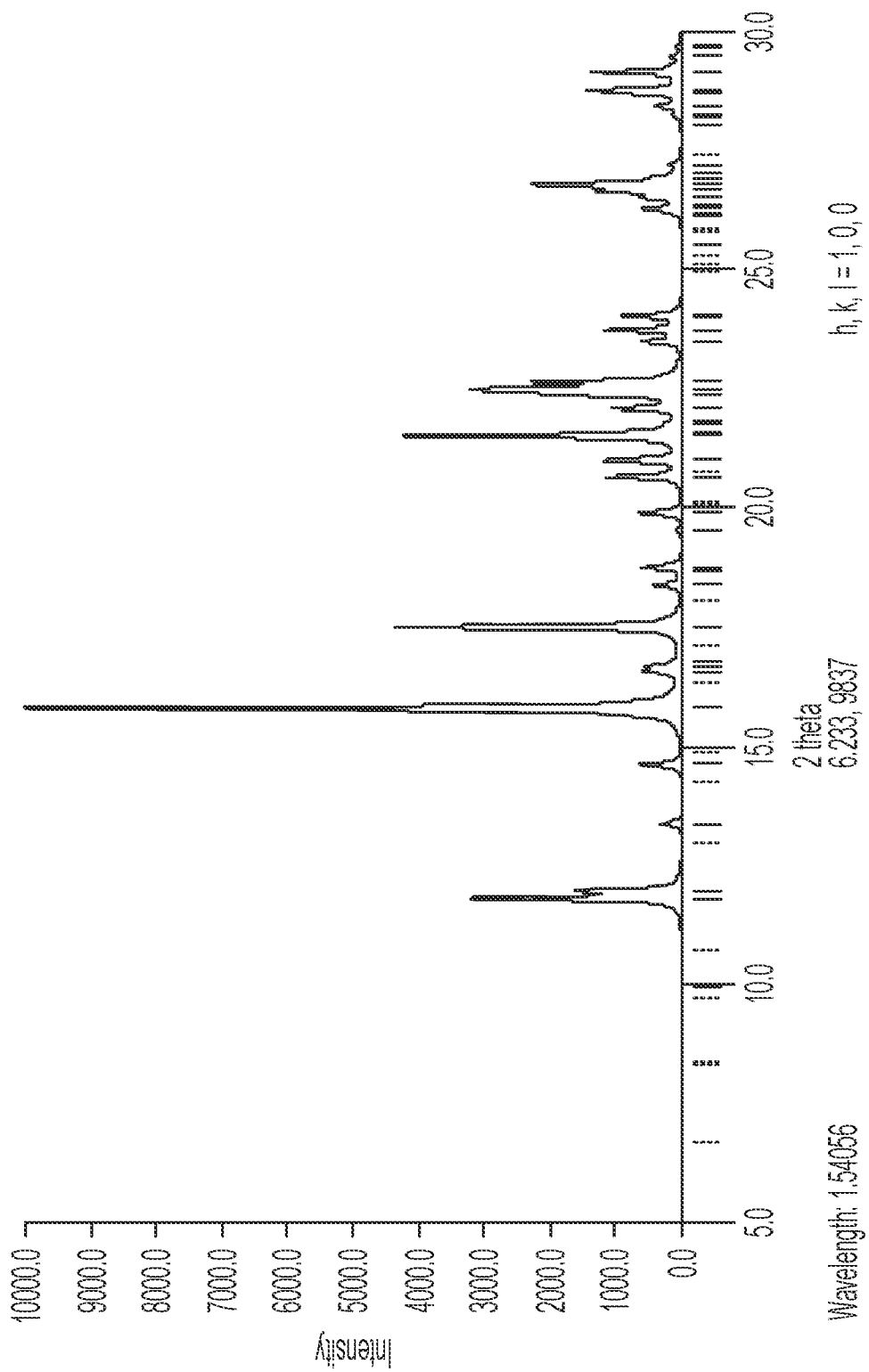
FIG. 9 shows a simulated X-ray powder diffraction pattern (XRPD) for crystalline form 1 of baeocystin generated from its single crystal data.

FIG. 9 shows a simulated X-ray powder diffraction pattern (XRPD) for crystalline form 1 of baeocystin generated from its single crystal data. Table 13 lists the angles, ° 2θ±0.2° 2θ, and d-spacing of the peaks identified in the experimental XRPD pattern of FIG. 9. The entire list of peaks, or a subset thereof, may be sufficient to characterize the cocrystal. For example, the cocrystal may be characterized by at least two peaks selected from the peaks at 15.8, 17.5, 21.5° 2θ±0.2° 2θ or their corresponding d-spacing as well as by a XRPD pattern substantially similar to FIG. 9.

TABLE 13

| d-spacing (Å) | 2(Theta deg) | Intensity |
|---|---|---|
| 8.92 | 9.91 | 189 |
| 7.49 | 11.81 | 48917 |
| 7.39 | 11.96 | 21696 |
| 6.61 | 13.37 | 6135 |

TABLE 13-continued

| d-spacing (Å) | 2(Theta deg) | Intensity |
|---|---|---|
| 6.06 | 14.61 | 15707 |
| 5.60 | 15.80 | 278077 |
| 5.35 | 16.57 | 15850 |
| 5.31 | 16.67 | 13588 |
| 5.28 | 16.79 | 881 |
| 5.06 | 17.51 | 154240 |
| 4.82 | 18.38 | 15481 |
| 4.75 | 18.68 | 125 |
| 4.73 | 18.76 | 24145 |
| 4.54 | 19.53 | 2974 |
| 4.46 | 19.90 | 28625 |
| 4.30 | 20.66 | 52851 |
| 4.23 | 21.01 | 56951 |
| 4.13 | 21.52 | 221786 |
| 4.08 | 21.77 | 5930 |
| 4.02 | 22.10 | 52074 |
| 3.97 | 22.39 | 83554 |
| 3.95 | 22.47 | 62406 |
| 3.95 | 22.51 | 114371 |
| 3.92 | 22.65 | 116844 |
| 3.78 | 23.50 | 36100 |
| 3.74 | 23.74 | 72262 |
| 3.70 | 24.02 | 34543 |
| 3.70 | 24.05 | 28530 |
| 3.49 | 25.51 | 309 |
| 3.41 | 26.14 | 83 |
| 3.39 | 26.27 | 46225 |
| 3.36 | 26.52 | 40463 |
| 3.34 | 26.67 | 86567 |
| 3.32 | 26.79 | 180296 |
| 3.31 | 26.94 | 23137 |
| 3.30 | 27.01 | 3306 |
| 3.27 | 27.21 | 12959 |
| 3.18 | 28.06 | 2767 |
| 3.16 | 28.18 | 2322 |
| 3.16 | 28.25 | 9559 |
| 3.14 | 28.44 | 34559 |
| 3.11 | 28.70 | 25104 |
| 3.11 | 28.72 | 3309 |
| 3.10 | 28.77 | 129604 |
| 3.06 | 29.16 | 134094 |
| 3.03 | 29.47 | 15062 |
| 3.01 | 29.66 | 682 |
| 3.01 | 29.70 | 6460 |

REFERENCES

Dolomanov, O. V., Bourhis, L. J., Gildea, R. J., Howard, J. A. K. & Puschmann, H. (2009). J. Appl. Cryst. 42, 339-341.

Sheldrick, G. M. (2015). Acta Cryst. C71, 3-8.

The invention claimed is:

1. A crystalline form 1 of methanol 5-[(3-{2-[bis(propan-2-yl) azaniumyl]ethyl}-1H-indol-4-yl)oxy]-5-oxopentanoate.

2. The crystalline form 1 of methanol 5-[(3-{2-[bis(propan-2-yl) azaniumyl]ethyl}-1H-indol-4-yl)oxy]-5-oxopentanoate according to claim 1, characterized by at least one of:

a monoclinic crystal system at a temperature of about 297 K;

a P2-Jc space group at a temperature of about 297 K; unit cell dimensions a=7.9531 (5) Å, b=13.4224 (7) Å, c=21.2015 (11) Å, and β=92.484 (2)°;

an x-ray powder diffraction (XRPD) pattern substantially similar to FIG. 3; and an X-ray powder diffraction pattern characterized by peaks at 8.3, 11.1, and 15.1°2θ±0.2°2θ.

3. A crystalline form 1 of ethanol 5-[(3-{2-[bis(propan-2-yl) azaniumyl]ethyl}-1H-indol-4-yl)oxy]-5-oxopentanoate.

4. The crystalline form 1 of ethanol 5-[(3-{2-[bis(propan-2-yl) azaniumyl]ethyl}-1H-indol-4-yl)oxy]-5-oxopentanoate according to claim 3, characterized by at least one of:
a monoclinic crystal system at a temperature of about 297 K;
a $P2_{1/c}$ space group at a temperature of about 297 K;
unit cell dimensions a=8.0087 (12) Å, b=13.7968 (17) Å, c=21.878 (3) Å, α=90°, β=90.749 (4)°, and γ=90°;
an X-ray powder diffraction pattern substantially similar to FIG. 6; and
an X-ray powder diffraction pattern characterized by at least two peaks selected from 8.1, 11.0, and 17.0°2θ± 0.2°2θ.

5. A composition comprising crystalline form 1 of methanol 5-[(3-{2-[bis(propan-2-yl) azaniumyl]ethyl}-1H-indol-4-yl)oxy]-5-oxopentanoate of claim 1 and an excipient.

6. A composition comprising crystalline form 1 of methanol 5-[(3-{2-[bis(propan-2-yl) azaniumyl]ethyl}-1H-indol-4-yl)oxy]-5-oxopentanoate of claim 1 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

7. A composition comprising crystalline form 1 of ethanol 5-[(3-{2-[bis(propan-2-yl) azaniumyl]ethyl}-1H-indol-4-yl)oxy]-5-oxopentanoate of claim 3 and an excipient.

8. A composition comprising crystalline form 1 of ethanol 5-[(3-{2-[bis(propan-2-yl) azaniumyl]ethyl}-1H-indol-4-yl)oxy]-5-oxopentanoate of claim 3 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

* * * * *